(12) United States Patent
Bosshard et al.

(10) Patent No.: US 10,772,665 B2
(45) Date of Patent: Sep. 15, 2020

(54) LOCKING STRUCTURES FOR AFFIXING BONE ANCHORS TO A BONE PLATE, AND RELATED SYSTEMS AND METHODS

(71) Applicant: DePuy Synthes Products, Inc., Raynham, MA (US)

(72) Inventors: Simon M. Bosshard, Bern (CH); Michael McGurk, Williamstown, NJ (US); Christopher Keegan, Hatboro, PA (US); Jesse B. Rush, Telford, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 162 days.

(21) Appl. No.: 15/940,761

(22) Filed: Mar. 29, 2018

(65) Prior Publication Data
US 2019/0298426 A1 Oct. 3, 2019

(51) Int. Cl.
*A61B 17/80* (2006.01)

(52) U.S. Cl.
CPC ...... *A61B 17/8057* (2013.01); *A61B 17/8052* (2013.01)

(58) Field of Classification Search
CPC . A61B 17/80; A61B 17/8004; A61B 17/8009; A61B 17/8019; A61B 17/8052; A61B 17/8061; A61B 17/8066; A61B 17/8071; A61B 17/8076
See application file for complete search history.

(56) References Cited

U.S. PATENT DOCUMENTS

| 327,296 | A | 9/1885 | Mcginnis |
| 1,105,105 | A | 7/1914 | O'n |
| 1,203,546 | A | 10/1916 | Parsons |
| 2,228,584 | A | 1/1941 | Piace |
| 2,352,297 | A | 6/1944 | Wales |

(Continued)

FOREIGN PATENT DOCUMENTS

| CA | 1112803 A | 11/1981 |
| CA | 2047521 A1 | 1/1992 |

(Continued)

OTHER PUBLICATIONS

European Patent Application No. 12006617.0: Extended European Search Report dated Jan. 21, 2013, 8 pages.

(Continued)

*Primary Examiner* — Eric S Gibson
(74) *Attorney, Agent, or Firm* — BakerHostetler

(57) ABSTRACT

A bone plate includes an upper surface, an opposed lower surface configured to face a bone, and at least one aperture extending through the bone plate from the upper to the lower surface along a central aperture axis. The aperture is defined by an interior surface of the bone plate. The interior surface defines a plurality of columns sequentially located about a circumference of the interior surface and a plurality of recesses located circumferentially between the columns. Each of the columns is configured to undergo deformation at least in a radial direction perpendicular to the central aperture axis responsive to engagement with a head of a locking bone screw that is receivable within the at least one aperture so as to lock the head to the bone plate. The plurality of columns comprises at least five columns.

20 Claims, 16 Drawing Sheets

(56) References Cited

U.S. PATENT DOCUMENTS

| | | |
|---|---|---|
| 2,414,882 A | 1/1947 | Longfellow |
| 2,443,363 A | 6/1948 | Kenneth et al. |
| 2,477,430 A | 7/1949 | Swanstrom |
| 2,496,126 A | 1/1950 | Haboush |
| 2,526,959 A | 10/1950 | Lorenzo |
| 2,612,159 A | 9/1952 | Collison |
| 2,627,855 A | 2/1953 | Price |
| 2,699,774 A | 1/1955 | Livingston |
| 2,772,676 A | 12/1956 | Pohl |
| 2,801,631 A | 8/1957 | Charnley |
| 2,846,701 A | 8/1958 | Bedford, Jr. |
| 2,874,691 A | 2/1959 | Mason |
| 3,025,853 A | 3/1962 | Mason |
| 3,229,743 A | 1/1966 | Derby |
| 3,263,949 A | 8/1966 | Conrad |
| 3,314,326 A | 4/1967 | Bedford, Jr. |
| 3,364,807 A | 1/1968 | Holton |
| 3,374,786 A | 3/1968 | Callender, Jr. |
| 3,388,732 A | 6/1968 | Holton |
| 3,463,148 A | 8/1969 | Treace |
| 3,489,143 A | 1/1970 | Halloran |
| 3,534,731 A | 10/1970 | Muller |
| 3,551,389 A | 12/1970 | Prince, Jr. |
| 3,552,389 A | 1/1971 | Allgower et al. |
| 3,561,437 A | 2/1971 | Orlich |
| 3,577,601 A | 5/1971 | Mariani et al. |
| 3,630,261 A | 12/1971 | Gley |
| 3,668,972 A | 6/1972 | Allgower et al. |
| 3,688,972 A | 9/1972 | Mahon |
| 3,695,259 A | 10/1972 | Yost |
| 3,695,618 A | 10/1972 | Woolley et al. |
| 3,716,050 A | 2/1973 | Johnston |
| 3,741,205 A | 6/1973 | Markolf et al. |
| 3,744,488 A | 7/1973 | Cox |
| 3,779,240 A | 12/1973 | Kondo |
| 3,782,374 A | 1/1974 | Fischer |
| 3,824,995 A | 7/1974 | Getscher et al. |
| 3,842,825 A | 10/1974 | Wagner |
| 3,877,339 A | 4/1975 | Muenchinger |
| RE28,841 E | 6/1976 | Martin et al. |
| 3,967,049 A | 6/1976 | Brandt |
| 3,996,834 A | 12/1976 | Reynolds |
| 3,996,931 A | 12/1976 | Callender, Jr. |
| 4,009,712 A | 3/1977 | Burstein et al. |
| 4,029,091 A | 6/1977 | Von et al. |
| 4,040,129 A | 8/1977 | Steinemann et al. |
| 4,095,591 A | 6/1978 | Graham et al. |
| 4,120,298 A | 10/1978 | Fixel |
| 4,172,452 A | 10/1979 | Forte et al. |
| 4,175,555 A | 11/1979 | Herbert |
| 4,219,015 A | 8/1980 | Steinemann |
| 4,236,512 A | 12/1980 | Aginsky |
| 4,263,904 A | 4/1981 | Judet |
| 4,269,180 A | 5/1981 | Dall et al. |
| 4,304,039 A | 12/1981 | Asmus |
| 4,338,926 A | 7/1982 | Kummer et al. |
| 4,355,198 A | 10/1982 | Gartland, Jr. |
| 4,379,451 A | 4/1983 | Getscher |
| 4,388,921 A | 6/1983 | Sutter et al. |
| 4,408,601 A | 10/1983 | Wenk |
| 4,429,690 A | 2/1984 | Angelino-Pievani |
| 4,438,762 A | 3/1984 | Kyle |
| 4,454,876 A | 6/1984 | Mears |
| RE31,628 E | 7/1984 | Allgower et al. |
| 4,484,570 A | 11/1984 | Sutter et al. |
| 4,484,750 A | 11/1984 | Scruggs |
| 4,488,543 A | 12/1984 | Tornier |
| 4,491,317 A | 1/1985 | Bansal |
| 4,493,317 A | 1/1985 | Klaue |
| 4,494,535 A | 1/1985 | Haig |
| 4,513,744 A | 4/1985 | Klaue |
| 4,537,185 A | 8/1985 | Stednitz |
| 4,565,193 A | 1/1986 | Streli |
| 4,580,225 A | 4/1986 | Thompson |
| 4,612,920 A | 9/1986 | Lower |
| 4,612,923 A | 9/1986 | Kronenthal |
| 4,616,638 A | 10/1986 | Griggs |
| 4,617,922 A | 10/1986 | Griggs |
| 4,621,629 A | 11/1986 | Koeneman |
| 4,628,923 A | 12/1986 | Medoff |
| 4,629,455 A | 12/1986 | Kanno |
| 4,630,985 A | 12/1986 | Simons |
| 4,651,724 A | 3/1987 | Berentey et al. |
| 4,657,001 A | 4/1987 | Fixel |
| 4,683,878 A | 8/1987 | Carter |
| 4,717,613 A | 1/1988 | Ottaviano |
| 4,747,613 A | 5/1988 | Brichoud et al. |
| 4,776,329 A | 10/1988 | Treharne |
| 4,776,330 A | 10/1988 | Chapman et al. |
| 4,781,183 A | 11/1988 | Casey et al. |
| 4,791,918 A | 12/1988 | Von Hasselbach |
| 4,794,918 A | 1/1989 | Wolter |
| 4,795,473 A | 1/1989 | Grimes |
| 4,800,874 A | 1/1989 | David et al. |
| 4,838,252 A | 6/1989 | Klaue |
| 4,848,328 A | 7/1989 | Laboureau et al. |
| 4,858,601 A | 8/1989 | Glisson |
| 4,867,144 A | 9/1989 | Karas et al. |
| 4,903,691 A | 2/1990 | Heinl |
| 4,905,680 A | 3/1990 | Tunc |
| 4,927,421 A | 5/1990 | Goble et al. |
| 4,955,886 A | 9/1990 | Pawluk |
| 4,957,496 A | 9/1990 | Schmidt |
| 4,957,497 A | 9/1990 | Hoogland et al. |
| 4,964,403 A | 10/1990 | Karas et al. |
| 4,966,599 A | 10/1990 | Pollock |
| 4,973,332 A | 11/1990 | Kummer |
| 4,973,333 A | 11/1990 | Treharne |
| 4,988,350 A | 1/1991 | Herzberg |
| 5,002,544 A | 3/1991 | Klaue et al. |
| 5,006,120 A | 4/1991 | Carter |
| 5,013,313 A | 5/1991 | Surer |
| 5,013,315 A | 5/1991 | Barrows |
| 5,015,248 A | 5/1991 | Burstein et al. |
| 5,027,904 A | 7/1991 | Miller et al. |
| 5,039,265 A | 8/1991 | Rath et al. |
| 5,041,113 A | 8/1991 | Biedermann et al. |
| 5,041,114 A | 8/1991 | Chapman et al. |
| 5,041,116 A | 8/1991 | Wilson |
| 5,053,036 A | 10/1991 | Perren et al. |
| 5,085,660 A | 2/1992 | Lin |
| 5,087,260 A | 2/1992 | Fixel |
| 5,108,399 A | 4/1992 | Eitenmuller et al. |
| 5,108,449 A | 4/1992 | Gray |
| 5,116,336 A | 5/1992 | Frigg |
| 5,127,914 A | 7/1992 | Calderale et al. |
| 5,129,901 A | 7/1992 | Decoste |
| 5,139,497 A | 8/1992 | Tilghman et al. |
| 5,147,361 A | 9/1992 | Ojima et al. |
| 5,147,363 A | 9/1992 | Haerle Anton |
| 5,151,103 A | 9/1992 | Tepic et al. |
| 5,152,794 A | 10/1992 | Davidson |
| 5,190,544 A | 3/1993 | Chapman et al. |
| 5,197,966 A | 3/1993 | Sommerkamp |
| 5,201,733 A | 4/1993 | Etheredge, III |
| 5,261,910 A | 11/1993 | Warden et al. |
| 5,269,784 A | 12/1993 | Mast |
| 5,275,601 A | 1/1994 | Gogolewski et al. |
| 5,290,281 A | 3/1994 | Tschakaloff |
| 5,300,074 A | 4/1994 | Frigg |
| 5,304,180 A | 4/1994 | Slocum |
| 5,306,275 A | 4/1994 | Bryan |
| 5,324,290 A | 6/1994 | Zdeblick et al. |
| 5,324,292 A | 6/1994 | Meyers |
| 5,336,224 A | 8/1994 | Selman |
| 5,356,410 A | 10/1994 | Pennig |
| 5,360,429 A | 11/1994 | Jeanson et al. |
| 5,360,448 A | 11/1994 | Thramann |
| 5,364,398 A | 11/1994 | Chapman et al. |
| 5,364,399 A | 11/1994 | Lowery et al. |
| 5,372,598 A | 12/1994 | Luhr et al. |
| 5,376,126 A | 12/1994 | Lin |
| 5,395,372 A | 3/1995 | Holt et al. |
| 5,403,136 A | 4/1995 | Mathys |

(56) References Cited

U.S. PATENT DOCUMENTS

| | | |
|---|---|---|
| 5,413,577 A | 5/1995 | Pollock |
| 5,429,641 A | 7/1995 | Gotfried |
| 5,433,719 A | 7/1995 | Pennig |
| 5,458,654 A | 10/1995 | Tepic |
| 5,462,547 A | 10/1995 | Weigum |
| 5,484,439 A | 1/1996 | Olson et al. |
| 5,514,138 A | 5/1996 | McCarthy |
| 5,520,690 A | 5/1996 | Errico et al. |
| 5,522,902 A | 6/1996 | Yuan et al. |
| 5,531,746 A | 7/1996 | Errico et al. |
| 5,534,032 A | 7/1996 | Hodorek |
| 5,558,674 A | 9/1996 | Heggeness et al. |
| 5,569,248 A | 10/1996 | Mathews |
| 5,571,109 A | 11/1996 | Bertagnoli |
| 5,571,198 A | 11/1996 | Drucker et al. |
| 5,586,985 A | 12/1996 | Putnam et al. |
| 5,591,168 A | 1/1997 | Judet et al. |
| 5,601,551 A | 2/1997 | Taylor et al. |
| 5,601,553 A | 2/1997 | Trebing et al. |
| 5,607,426 A | 3/1997 | Ralph et al. |
| 5,607,427 A | 3/1997 | Tschakaloff |
| 5,607,428 A | 3/1997 | Lin |
| 5,620,445 A | 4/1997 | Brosnahan et al. |
| 5,647,872 A | 7/1997 | Gilbert et al. |
| 5,655,089 A | 8/1997 | Bucci |
| 5,658,339 A | 8/1997 | Tronzo et al. |
| 5,662,655 A | 9/1997 | Laboureau et al. |
| 5,674,222 A | 10/1997 | Berger et al. |
| 5,676,667 A | 10/1997 | Hausman |
| 5,681,311 A | 10/1997 | Foley et al. |
| D385,963 S | 11/1997 | Hansson |
| 5,690,633 A | 11/1997 | Taylor et al. |
| 5,693,055 A | 12/1997 | Zahiri et al. |
| 5,702,396 A | 12/1997 | Hoenig et al. |
| 5,702,399 A | 12/1997 | Kilpela et al. |
| 5,709,682 A | 1/1998 | Medoff |
| 5,709,686 A | 1/1998 | Talos et al. |
| 5,709,687 A | 1/1998 | Pennig |
| 5,718,704 A | 2/1998 | Medoff |
| 5,718,705 A | 2/1998 | Sammarco |
| 5,728,099 A | 3/1998 | Tellman et al. |
| 5,733,287 A | 3/1998 | Tepic et al. |
| 5,735,853 A | 4/1998 | Olerud |
| 5,741,256 A | 4/1998 | Bresina |
| 5,741,258 A | 4/1998 | Klaue et al. |
| 5,743,912 A | 4/1998 | Lahille et al. |
| 5,749,872 A | 5/1998 | Kyle et al. |
| 5,766,175 A | 6/1998 | Martinotti |
| 5,772,662 A | 6/1998 | Chapman et al. |
| 5,779,706 A | 7/1998 | Tschakaloff |
| 5,785,713 A | 7/1998 | Jobe |
| 5,797,916 A | 8/1998 | McDowell |
| 5,800,553 A | 9/1998 | Albrektsson et al. |
| 5,810,821 A | 9/1998 | Vandewalle |
| 5,810,822 A | 9/1998 | Mortier |
| 5,810,823 A | 9/1998 | Klaue et al. |
| 5,827,286 A | 10/1998 | Incavo et al. |
| 5,853,413 A | 12/1998 | Carter et al. |
| 5,921,988 A | 7/1999 | Legrand |
| 5,928,084 A | 7/1999 | Green |
| 5,931,801 A | 8/1999 | Burbank et al. |
| 5,931,839 A | 8/1999 | Medoff |
| 5,938,664 A | 8/1999 | Winquist et al. |
| 5,954,722 A | 9/1999 | Bono |
| 5,961,524 A | 10/1999 | Crombie |
| 5,968,046 A | 10/1999 | Castleman |
| 5,968,047 A | 10/1999 | Reed |
| 5,973,223 A | 10/1999 | Tellman et al. |
| 5,976,139 A | 11/1999 | Bramlet |
| 5,976,141 A | 11/1999 | Haag et al. |
| 5,989,255 A | 11/1999 | Pepper et al. |
| 5,999,940 A | 12/1999 | Ranger |
| 6,001,099 A | 12/1999 | Huebner |
| 6,007,535 A | 12/1999 | Rayhack et al. |
| 6,022,352 A | 2/2000 | Vandewalle |
| 6,030,162 A | 2/2000 | Huebner |
| 6,030,389 A | 2/2000 | Wagner et al. |
| 6,059,785 A | 5/2000 | Schavan et al. |
| 6,066,141 A | 5/2000 | Dall et al. |
| 6,096,040 A | 8/2000 | Esser |
| 6,113,603 A | 9/2000 | Medoff |
| 6,129,728 A | 10/2000 | Schumacher et al. |
| 6,129,730 A | 10/2000 | Bono et al. |
| 6,152,927 A | 11/2000 | Farris et al. |
| 6,155,756 A | 12/2000 | Mericle et al. |
| 6,183,474 B1 | 2/2001 | Bramlet et al. |
| 6,183,475 B1 | 2/2001 | Lester et al. |
| 6,187,007 B1 | 2/2001 | Frigg et al. |
| 6,206,881 B1 | 3/2001 | Frigg et al. |
| 6,221,073 B1 | 4/2001 | Weiss et al. |
| 6,221,075 B1 | 4/2001 | Toermala et al. |
| D443,060 S | 5/2001 | Benirschke et al. |
| 6,224,602 B1 | 5/2001 | Hayes |
| 6,228,085 B1 | 5/2001 | Theken et al. |
| 6,235,032 B1 | 5/2001 | Link |
| 6,235,033 B1 | 5/2001 | Brace et al. |
| 6,258,250 B1 | 7/2001 | Weissenbacher et al. |
| 6,261,291 B1 | 7/2001 | Talaber et al. |
| 6,283,969 B1 | 9/2001 | Grusin et al. |
| 6,287,309 B1 | 9/2001 | Baccelli et al. |
| 6,290,703 B1 | 9/2001 | Ganem |
| 6,306,136 B1 | 10/2001 | Baccelli |
| 6,306,140 B1 | 10/2001 | Siddiqui |
| 6,322,562 B1 | 11/2001 | Wolter |
| 6,325,803 B1 | 12/2001 | Schumacher et al. |
| 6,338,734 B1 | 1/2002 | Burke et al. |
| 6,342,055 B1 | 1/2002 | Eisermann et al. |
| 6,348,052 B1 | 2/2002 | Sammarco |
| 6,350,265 B1 | 2/2002 | Blaustein et al. |
| 6,355,041 B1 | 3/2002 | Martin |
| 6,355,042 B2 | 3/2002 | Winquist et al. |
| 6,358,250 B1 | 3/2002 | Orbay |
| 6,364,882 B1 | 4/2002 | Orbay |
| 6,375,657 B1 | 4/2002 | Doubler et al. |
| 6,379,359 B1 | 4/2002 | Dahners |
| D458,374 S | 6/2002 | Bryant et al. |
| D458,683 S | 6/2002 | Bryant et al. |
| D458,684 S | 6/2002 | Bryant et al. |
| D458,996 S | 6/2002 | Bryant et al. |
| 6,423,064 B1 | 7/2002 | Kluger |
| 6,440,131 B1 | 8/2002 | Haidukewych |
| 6,440,135 B2 | 8/2002 | Orbay et al. |
| D463,557 S | 9/2002 | Bryant et al. |
| D463,558 S | 9/2002 | Bryant et al. |
| D463,559 S | 9/2002 | Bryant et al. |
| 6,454,769 B2 | 9/2002 | Wagner et al. |
| 6,454,770 B1 | 9/2002 | Klaue |
| D464,136 S | 10/2002 | Bryant et al. |
| D464,731 S | 10/2002 | Bryant et al. |
| 6,468,278 B1 | 10/2002 | Mueckter |
| 6,488,685 B1 | 12/2002 | Manderson |
| D469,532 S | 1/2003 | Bryant et al. |
| D469,533 S | 1/2003 | Bryant et al. |
| D469,534 S | 1/2003 | Bryant et al. |
| 6,503,252 B2 | 1/2003 | Hansson |
| 6,503,281 B1 | 1/2003 | Mallory |
| 6,508,819 B1 | 1/2003 | Orbay |
| D469,874 S | 2/2003 | Bryant et al. |
| D469,875 S | 2/2003 | Bryant et al. |
| D470,588 S | 2/2003 | Bryant et al. |
| 6,525,525 B1 | 2/2003 | Azinger |
| 6,527,776 B1 | 3/2003 | Michelson |
| 6,533,789 B1 | 3/2003 | Hall et al. |
| 6,565,525 B1 | 5/2003 | Burbank et al. |
| 6,565,569 B1 | 5/2003 | Assaker et al. |
| 6,575,975 B2 | 6/2003 | Brace et al. |
| 6,602,256 B1 | 8/2003 | Hayes |
| 6,605,090 B1 | 8/2003 | Trieu et al. |
| D479,331 S | 9/2003 | Pike et al. |
| D480,141 S | 9/2003 | Benirschke et al. |
| 6,623,486 B1 | 9/2003 | Weaver et al. |
| 6,648,891 B2 | 11/2003 | Kim |
| 6,666,868 B2 | 12/2003 | Fallin |
| 6,669,700 B1 | 12/2003 | Farris et al. |

(56) References Cited

U.S. PATENT DOCUMENTS

| | | | |
|---|---|---|---|
| 6,669,701 B2 | 12/2003 | Steiner et al. | |
| 6,712,820 B2 | 3/2004 | Orbay | |
| 6,719,759 B2 | 4/2004 | Wagner et al. | |
| 6,730,091 B1 | 5/2004 | Pfefferle et al. | |
| 6,767,351 B2 | 7/2004 | Orbay et al. | |
| 6,835,197 B2 | 12/2004 | Roth et al. | |
| 6,863,483 B2 | 3/2005 | Koenig et al. | |
| 6,866,665 B2 | 3/2005 | Orbay | |
| 6,875,215 B2 | 4/2005 | Taras et al. | |
| 6,893,443 B2 | 5/2005 | Frigg et al. | |
| 6,955,677 B2 | 10/2005 | Dahners | |
| 6,974,461 B1 | 12/2005 | Wolter | |
| 7,001,388 B2 | 2/2006 | Orbay et al. | |
| 7,044,953 B2 | 5/2006 | Capanni | |
| 7,128,744 B2 | 10/2006 | Weaver et al. | |
| 7,169,149 B1 | 1/2007 | Hajianpour | |
| 7,179,260 B2 | 2/2007 | Gerlach et al. | |
| 7,229,445 B2 | 6/2007 | Hayeck et al. | |
| 7,282,053 B2 | 10/2007 | Orbay | |
| 7,294,130 B2 | 11/2007 | Orbay | |
| 7,309,340 B2 | 12/2007 | Fallin et al. | |
| 7,316,687 B2 | 1/2008 | Aikins et al. | |
| 7,338,491 B2 | 3/2008 | Baker et al. | |
| 7,341,589 B2 | 3/2008 | Weaver et al. | |
| 7,354,441 B2 | 4/2008 | Frigg | |
| 7,517,350 B2 | 4/2009 | Weiner et al. | |
| 7,527,639 B2 | 5/2009 | Orbay et al. | |
| 7,537,596 B2 | 5/2009 | Jensen | |
| 7,635,381 B2 | 12/2009 | Orbay | |
| 7,637,928 B2 | 12/2009 | Fernandez | |
| 7,641,677 B2 | 1/2010 | Weiner et al. | |
| 7,695,472 B2 | 4/2010 | Young | |
| 7,695,502 B2 | 4/2010 | Orbay et al. | |
| 7,766,916 B2 | 8/2010 | Leyden et al. | |
| 7,771,433 B2 | 8/2010 | Orbay et al. | |
| 7,771,457 B2 | 8/2010 | Kay et al. | |
| 7,776,076 B2 | 8/2010 | Grady | |
| 7,776,916 B2 | 8/2010 | Freeman et al. | |
| 7,857,838 B2 | 12/2010 | Orbay | |
| 7,867,260 B2 | 1/2011 | Meyer et al. | |
| 7,905,909 B2 | 3/2011 | Orbay et al. | |
| 7,951,176 B2 | 5/2011 | Grady et al. | |
| 8,075,561 B2 | 12/2011 | Wolter | |
| 8,092,505 B2 | 1/2012 | Sommers | |
| 8,118,846 B2 * | 2/2012 | Leither | A61B 17/8057 606/280 |
| 8,118,848 B2 | 2/2012 | Ducharme et al. | |
| 8,337,535 B2 * | 12/2012 | White | A61B 17/8605 606/289 |
| 8,343,196 B2 * | 1/2013 | Schneider | A61B 17/8033 606/286 |
| 8,403,967 B2 | 3/2013 | Orbay | |
| 8,506,607 B2 * | 8/2013 | Eckhof | A61B 17/8057 606/286 |
| 8,518,042 B2 | 8/2013 | Winslow et al. | |
| 8,556,945 B2 | 10/2013 | Orbay | |
| 8,574,268 B2 | 11/2013 | Chan et al. | |
| 8,579,946 B2 | 11/2013 | Orbay | |
| 8,641,744 B2 | 2/2014 | Weaver et al. | |
| 8,758,346 B2 * | 6/2014 | Koay | A61B 17/8057 606/282 |
| 8,814,918 B2 | 8/2014 | Orbay et al. | |
| 8,845,698 B2 | 9/2014 | Schneider | |
| 8,852,245 B2 | 10/2014 | Schneider | |
| 8,876,873 B2 | 11/2014 | Schneider | |
| 8,894,693 B2 | 11/2014 | Petit et al. | |
| 8,940,029 B2 | 1/2015 | Leung et al. | |
| 9,072,558 B2 | 7/2015 | Orbay | |
| 9,107,711 B2 | 8/2015 | Hainard | |
| 9,168,075 B2 | 10/2015 | Dell Oca | |
| 9,265,542 B2 | 2/2016 | Koay et al. | |
| 9,277,947 B2 | 3/2016 | Koay et al. | |
| 9,295,505 B2 | 3/2016 | Schneider | |
| 9,308,034 B2 | 4/2016 | Grady | |
| 9,314,284 B2 * | 4/2016 | Chan | A61B 17/1728 |
| 9,387,022 B2 * | 7/2016 | Koay | A61B 17/8057 |
| 9,433,454 B2 * | 9/2016 | Paolino | A61B 17/8057 |
| 9,498,267 B2 * | 11/2016 | Pfeiffer | A61B 17/8057 |
| 9,510,880 B2 * | 12/2016 | Terrill | A61B 17/8052 |
| 9,554,909 B2 | 1/2017 | Donner et al. | |
| 9,855,083 B2 | 1/2018 | Mighell et al. | |
| 9,867,643 B2 * | 1/2018 | Terrill | A61B 17/8057 |
| 9,931,148 B2 | 4/2018 | Grady | |
| 2001/0000186 A1 | 4/2001 | Bramlet et al. | |
| 2001/0011172 A1 | 8/2001 | Orbay et al. | |
| 2001/0012940 A1 | 8/2001 | Tunc | |
| 2002/0013587 A1 | 1/2002 | Winquist et al. | |
| 2002/0032446 A1 | 3/2002 | Orbay | |
| 2002/0045901 A1 | 4/2002 | Wagner et al. | |
| 2002/0049445 A1 | 4/2002 | Hall et al. | |
| 2002/0062127 A1 | 5/2002 | Schumacher et al. | |
| 2002/0065516 A1 | 5/2002 | Winquist et al. | |
| 2002/0128654 A1 | 9/2002 | Steger et al. | |
| 2002/0143337 A1 | 10/2002 | Orbay et al. | |
| 2002/0143338 A1 | 10/2002 | Orbay et al. | |
| 2002/0156474 A1 | 10/2002 | Wack et al. | |
| 2002/0183752 A1 | 12/2002 | Steiner et al. | |
| 2002/0183753 A1 | 12/2002 | Manderson | |
| 2003/0040748 A1 | 2/2003 | Aikins et al. | |
| 2003/0055435 A1 | 3/2003 | Barrick | |
| 2003/0060827 A1 | 3/2003 | Coughlin | |
| 2003/0083660 A1 | 5/2003 | Orbay | |
| 2003/0083661 A1 | 5/2003 | Orbay et al. | |
| 2003/0105461 A1 | 6/2003 | Putnam | |
| 2003/0125738 A1 | 7/2003 | Khanna | |
| 2003/0135212 A1 | 7/2003 | Y Chow | |
| 2003/0135216 A1 | 7/2003 | Sevrain | |
| 2004/0030339 A1 | 2/2004 | Wack et al. | |
| 2004/0049193 A1 | 3/2004 | Capanni | |
| 2004/0059334 A1 | 3/2004 | Weaver et al. | |
| 2004/0059335 A1 | 3/2004 | Weaver et al. | |
| 2004/0073218 A1 | 4/2004 | Dahners | |
| 2004/0097937 A1 | 5/2004 | Pike et al. | |
| 2004/0097941 A1 | 5/2004 | Weiner et al. | |
| 2004/0111089 A1 | 6/2004 | Stevens et al. | |
| 2004/0215198 A1 | 10/2004 | Marnay et al. | |
| 2004/0254579 A1 | 12/2004 | Buhren et al. | |
| 2004/0260291 A1 | 12/2004 | Jensen | |
| 2004/0260306 A1 * | 12/2004 | Fallin | A61B 17/7059 606/104 |
| 2005/0015089 A1 | 1/2005 | Young et al. | |
| 2005/0049593 A1 | 3/2005 | Duong et al. | |
| 2005/0080421 A1 | 4/2005 | Weaver et al. | |
| 2005/0085818 A1 | 4/2005 | Huebner | |
| 2005/0107796 A1 | 5/2005 | Gerlach et al. | |
| 2005/0165400 A1 | 7/2005 | Fernandez | |
| 2005/0171544 A1 | 8/2005 | Falkner, Jr. | |
| 2005/0187555 A1 | 8/2005 | Biedermann et al. | |
| 2005/0216001 A1 | 9/2005 | David | |
| 2005/0261688 A1 | 11/2005 | Grady et al. | |
| 2005/0277937 A1 | 12/2005 | Leung et al. | |
| 2006/0004361 A1 | 1/2006 | Hayeck et al. | |
| 2006/0058797 A1 | 3/2006 | Mathieu et al. | |
| 2006/0200151 A1 | 9/2006 | Ducharme et al. | |
| 2006/0217722 A1 | 9/2006 | Dutoit et al. | |
| 2006/0235400 A1 * | 10/2006 | Schneider | A61B 17/8057 606/287 |
| 2006/0264946 A1 | 11/2006 | Young | |
| 2007/0016205 A1 | 1/2007 | Beutter et al. | |
| 2007/0083207 A1 | 4/2007 | Ziolo et al. | |
| 2007/0088360 A1 | 4/2007 | Orbay et al. | |
| 2007/0162016 A1 | 7/2007 | Matityahu | |
| 2007/0206244 A1 | 9/2007 | Kobayashi | |
| 2007/0208378 A1 | 9/2007 | Bonutti et al. | |
| 2007/0225716 A1 | 9/2007 | Deffenbaugh et al. | |
| 2007/0260244 A1 | 11/2007 | Wolter | |
| 2007/0276386 A1 | 11/2007 | Gerlach et al. | |
| 2007/0276402 A1 | 11/2007 | Frankel et al. | |
| 2008/0065070 A1 | 3/2008 | Freid et al. | |
| 2008/0132960 A1 | 6/2008 | Weaver et al. | |
| 2008/0140130 A1 * | 6/2008 | Chan | A61B 17/1728 606/280 |
| 2008/0208259 A1 | 8/2008 | Gilbert et al. | |

(56) References Cited

U.S. PATENT DOCUMENTS

| | | |
|---|---|---|
| 2008/0234749 A1 | 9/2008 | Forstein |
| 2008/0234752 A1 | 9/2008 | Dahners |
| 2008/0300637 A1* | 12/2008 | Austin .................. A61B 17/74 606/290 |
| 2009/0018557 A1 | 1/2009 | Pisharodi |
| 2009/0018588 A1* | 1/2009 | Eckhof .............. A61B 17/8057 606/280 |
| 2009/0036933 A1 | 2/2009 | Dube et al. |
| 2009/0076553 A1 | 3/2009 | Wolter |
| 2009/0076554 A1 | 3/2009 | Huebner et al. |
| 2009/0099610 A1 | 4/2009 | Johnson et al. |
| 2009/0118768 A1 | 5/2009 | Sixto et al. |
| 2009/0143824 A1 | 6/2009 | Austin et al. |
| 2009/0143825 A1 | 6/2009 | Graham et al. |
| 2009/0216242 A1 | 8/2009 | Riemer et al. |
| 2009/0281543 A1 | 11/2009 | Orbay et al. |
| 2009/0287258 A1 | 11/2009 | Vannemreddy |
| 2009/0292318 A1 | 11/2009 | White et al. |
| 2009/0312803 A1 | 12/2009 | Austin et al. |
| 2010/0016858 A1* | 1/2010 | Michel ............... A61B 17/8057 606/70 |
| 2010/0030277 A1 | 2/2010 | Haidukewych et al. |
| 2010/0057086 A1 | 3/2010 | Price et al. |
| 2010/0076496 A1 | 3/2010 | Fernandez |
| 2010/0094357 A1 | 4/2010 | Wallenstein et al. |
| 2010/0100134 A1 | 4/2010 | Mocanu |
| 2010/0137919 A1 | 6/2010 | Wolter |
| 2010/0274296 A1 | 10/2010 | Appenzeller et al. |
| 2010/0312285 A1* | 12/2010 | White ................ A61B 17/8057 606/289 |
| 2010/0312286 A1* | 12/2010 | Dell'Oca .......... A61B 17/8057 606/291 |
| 2011/0046681 A1 | 2/2011 | Prandi et al. |
| 2011/0087229 A1 | 4/2011 | Kubiak et al. |
| 2011/0106081 A1 | 5/2011 | Graham et al. |
| 2011/0224671 A1* | 9/2011 | Koay ................. A61B 17/8014 606/70 |
| 2011/0301608 A1* | 12/2011 | Roth .................. A61B 17/8052 606/70 |
| 2012/0143193 A1* | 6/2012 | Hulliger ............ A61B 17/8057 606/70 |
| 2012/0197307 A1 | 8/2012 | Fritzinger et al. |
| 2012/0245642 A1 | 9/2012 | Giannoudis et al. |
| 2013/0096631 A1 | 4/2013 | Leung et al. |
| 2013/0116735 A1* | 5/2013 | Schneider .......... A61B 17/8057 606/291 |
| 2013/0172943 A1 | 7/2013 | Austin et al. |
| 2013/0190828 A1* | 7/2013 | Schneider .......... A61B 17/8052 606/286 |
| 2013/0197589 A1 | 8/2013 | Schneider |
| 2013/0245699 A1 | 9/2013 | Orbay et al. |
| 2013/0261675 A1 | 10/2013 | Fritzinger |
| 2014/0005728 A1* | 1/2014 | Koay ................. A61B 17/8057 606/281 |
| 2014/0018862 A1* | 1/2014 | Koay ................. A61B 17/8057 606/281 |
| 2014/0180345 A1 | 6/2014 | Chan et al. |
| 2014/0207194 A1 | 7/2014 | Wolter |
| 2014/0236154 A1 | 8/2014 | Liao et al. |
| 2014/0271028 A1 | 9/2014 | Arnett |
| 2014/0277180 A1 | 9/2014 | Paolino et al. |
| 2014/0316473 A1* | 10/2014 | Pfeiffer ............. A61B 17/8014 606/291 |
| 2014/0324108 A1 | 10/2014 | Orbay et al. |
| 2015/0051651 A1* | 2/2015 | Terrill ............... A61B 17/8605 606/289 |
| 2015/0105829 A1 | 4/2015 | Laird |
| 2015/0257802 A1* | 9/2015 | Wolf .................... A61B 17/80 606/291 |
| 2015/0327897 A1* | 11/2015 | Hulliger ............. A61B 17/8057 606/291 |
| 2015/0327898 A1* | 11/2015 | Martin ............... A61B 17/8057 606/291 |
| 2015/0359575 A1* | 12/2015 | Pech .................. A61B 17/8605 606/291 |
| 2016/0074081 A1 | 3/2016 | Weaver et al. |
| 2016/0089191 A1 | 3/2016 | Pak et al. |
| 2016/0143676 A1 | 5/2016 | Koay et al. |
| 2016/0166294 A1 | 6/2016 | Schneider |
| 2016/0242829 A1 | 8/2016 | Kim et al. |
| 2016/0278826 A1 | 9/2016 | Epperly |
| 2016/0310184 A1* | 10/2016 | Kazanovicz ....... A61B 17/8061 |
| 2016/0317205 A1* | 11/2016 | Baker ................ A61B 17/8052 |
| 2016/0367299 A1 | 12/2016 | Paolino et al. |
| 2017/0265915 A1 | 9/2017 | Langdale et al. |
| 2017/0319248 A1 | 11/2017 | Milella et al. |
| 2018/0008326 A1 | 1/2018 | Hulliger et al. |
| 2018/0036049 A1 | 2/2018 | Kobayashi |
| 2018/0064476 A1* | 3/2018 | Lopez ................ A61B 17/8061 |
| 2018/0064477 A1* | 3/2018 | Lopez ................ A61B 17/8033 |
| 2018/0064479 A1* | 3/2018 | Lopez ................ A61B 17/8061 |
| 2018/0132913 A1 | 5/2018 | Davison et al. |
| 2018/0235681 A1 | 8/2018 | Chambers et al. |
| 2019/0298426 A1* | 10/2019 | Bosshard .......... A61B 17/8057 |

FOREIGN PATENT DOCUMENTS

| | | |
|---|---|---|
| CA | 2536960 A1 | 3/2005 |
| CH | 611147 A5 | 5/1979 |
| CH | 670755 A5 | 7/1989 |
| CH | 672245 A5 | 11/1989 |
| CH | 675531 A5 | 10/1990 |
| CN | 1486162 A | 3/2004 |
| DE | 2933637 A1 | 4/1980 |
| DE | 3442004 C1 | 4/1986 |
| DE | 3722852 A1 | 1/1989 |
| DE | 3743638 A1 | 7/1989 |
| DE | 4004941 A1 | 8/1990 |
| DE | 3942326 A1 | 6/1991 |
| DE | 4201531 A1 | 7/1993 |
| DE | 4341980 A1 | 6/1995 |
| DE | 4343117 A1 | 6/1995 |
| DE | 4438264 A1 | 3/1996 |
| DE | 19636733 A1 | 4/1997 |
| DE | 19629011 A1 | 1/1998 |
| DE | 9321544 U1 | 9/1999 |
| DE | 19832513 A1 | 2/2000 |
| DE | 19858889 A1 | 6/2000 |
| DE | 10015734 A1 | 9/2001 |
| DE | 10125092 A1 | 12/2001 |
| DE | 20309361 U1 | 9/2003 |
| DE | 20317651 U1 | 3/2004 |
| DE | 10319781 B3 | 8/2004 |
| DE | 102004009429 A1 | 9/2005 |
| DE | 102005042766 A1 | 1/2007 |
| DE | 202006019220 U1 | 5/2007 |
| DE | 202008000914 U1 | 3/2008 |
| DE | 202007017159 U1 | 5/2008 |
| DE | 102010048052 | 4/2012 |
| DE | 102016112845 A1 | 1/2018 |
| DE | 202014011161 U1 | 3/2018 |
| EP | 0053999 A1 | 6/1982 |
| EP | 0158030 A1 | 10/1985 |
| EP | 0180532 A1 | 5/1986 |
| EP | 0207884 A2 | 1/1987 |
| EP | 0241914 A2 | 10/1987 |
| EP | 0244782 A1 | 11/1987 |
| EP | 0251583 A2 | 1/1988 |
| EP | 0266146 A2 | 5/1988 |
| EP | 0274713 A1 | 7/1988 |
| EP | 0290138 A2 | 11/1988 |
| EP | 0291632 A1 | 11/1988 |
| EP | 0299160 A1 | 1/1989 |
| EP | 0337288 A1 | 10/1989 |
| EP | 0360139 A2 | 3/1990 |
| EP | 0381462 A2 | 8/1990 |
| EP | 0382256 A1 | 8/1990 |
| EP | 0410309 A1 | 1/1991 |
| EP | 0436885 A2 | 7/1991 |
| EP | 0471418 A1 | 2/1992 |
| EP | 0506420 A1 | 9/1992 |
| EP | 0515828 A1 | 12/1992 |

(56) References Cited

FOREIGN PATENT DOCUMENTS

| | | |
|---|---|---|
| EP | 0530585 A2 | 3/1993 |
| EP | 0532421 A1 | 3/1993 |
| EP | 0546460 A1 | 6/1993 |
| EP | 0649635 A1 | 4/1995 |
| EP | 0668059 A1 | 8/1995 |
| EP | 0760231 A1 | 3/1997 |
| EP | 0848600 A1 | 6/1998 |
| EP | 1132052 A2 | 9/2001 |
| EP | 1468655 A2 | 10/2004 |
| EP | 1604619 A1 | 12/2005 |
| EP | 1658015 A1 | 5/2006 |
| EP | 1712197 A1 | 10/2006 |
| EP | 1741397 A2 | 1/2007 |
| EP | 1767160 A2 | 3/2007 |
| EP | 1878394 A2 | 1/2008 |
| EP | 1568329 A1 | 8/2008 |
| EP | 2529685 A1 | 12/2012 |
| FR | 0742618 A | 3/1933 |
| FR | 2233973 A1 | 1/1975 |
| FR | 2405062 A1 | 5/1979 |
| FR | 2405705 A1 | 5/1979 |
| FR | 2405706 A1 | 5/1979 |
| FR | 2496429 A3 | 6/1982 |
| FR | 2606268 A1 | 5/1988 |
| FR | 2622431 A1 | 5/1989 |
| FR | 2650500 A1 | 2/1991 |
| FR | 2671966 A3 | 7/1992 |
| FR | 2674118 A1 | 9/1992 |
| FR | 2677876 A1 | 12/1992 |
| FR | 2706763 A1 | 12/1994 |
| FR | 2739151 A1 | 3/1997 |
| FR | 2757370 A1 | 6/1998 |
| FR | 2802082 A1 | 6/2001 |
| GB | 0997733 A | 7/1965 |
| GB | 1237405 A | 6/1971 |
| GB | 1250413 A | 10/1971 |
| GB | 1312189 A | 4/1973 |
| GB | 1385398 A | 2/1975 |
| GB | 2017502 A | 10/1979 |
| GB | 1575194 A | 9/1980 |
| GB | 2090745 A | 7/1982 |
| GB | 2245498 A | 1/1992 |
| GB | 2257913 A | 1/1993 |
| JP | 02-121652 A | 5/1990 |
| JP | 03-058150 | 3/1991 |
| JP | 03-158150 | 7/1991 |
| JP | 04-138152 A | 5/1992 |
| JP | 06-045941 | 2/1994 |
| JP | 06-125918 | 5/1994 |
| JP | 06-245941 | 9/1994 |
| JP | 08-098846 | 4/1996 |
| JP | 08-126650 | 5/1996 |
| JP | 08-257034 | 10/1996 |
| JP | 08-266562 A | 10/1996 |
| JP | 09-108237 | 4/1997 |
| JP | 10-118096 A | 5/1998 |
| JP | 11-076259 | 3/1999 |
| JP | 11-299804 | 8/1999 |
| JP | 11-276501 | 10/1999 |
| JP | 11-512004 | 10/1999 |
| JP | 11-318930 | 11/1999 |
| JP | 2000-000247 A | 1/2000 |
| JP | 2000-152944 A | 6/2000 |
| JP | 2001-149379 A | 6/2001 |
| JP | 2001-161704 A | 6/2001 |
| JP | 2001-514039 | 9/2001 |
| JP | 2001-525701 | 12/2001 |
| JP | 2001-525702 | 12/2001 |
| JP | 2002-095673 A | 4/2002 |
| JP | 2002-232185 A | 8/2002 |
| JP | 2002-532185 A | 10/2002 |
| JP | 2002-345836 A | 12/2002 |
| JP | 2002-542875 | 12/2002 |
| JP | 2003-024344 A | 1/2003 |
| JP | 2003-038508 A | 2/2003 |
| JP | 2003-038509 A | 2/2003 |
| JP | 2003-509107 | 3/2003 |
| JP | 2003-521303 | 7/2003 |
| KR | 10-2007-0034449 A | 3/2007 |
| KR | 10-2008-0028917 A | 4/2008 |
| SU | 1037911 | 8/1983 |
| SU | 1279626 A1 | 12/1986 |
| WO | 87/00419 A1 | 1/1987 |
| WO | 87/06982 A1 | 11/1987 |
| WO | 88/03781 A1 | 6/1988 |
| WO | 92/11819 A1 | 7/1992 |
| WO | 93/11714 A1 | 6/1993 |
| WO | 93/15678 A1 | 8/1993 |
| WO | 93/22982 A1 | 11/1993 |
| WO | 94/02073 A1 | 2/1994 |
| WO | 95/32674 A1 | 12/1995 |
| WO | 96/17556 A1 | 6/1996 |
| WO | 96/25892 A1 | 8/1996 |
| WO | 96/29948 A1 | 10/1996 |
| WO | 97/08999 A1 | 3/1997 |
| WO | 97/09000 A1 | 3/1997 |
| WO | 97/20514 A1 | 6/1997 |
| WO | 98/02105 A1 | 1/1998 |
| WO | 98/05263 A1 | 2/1998 |
| WO | 98/51226 A2 | 11/1998 |
| WO | 98/51368 A1 | 11/1998 |
| WO | 99/25266 A1 | 5/1999 |
| WO | 99/44529 A1 | 9/1999 |
| WO | 00/53110 A1 | 9/2000 |
| WO | 00/53111 A1 | 9/2000 |
| WO | 00/66012 A1 | 11/2000 |
| WO | 01/19267 A1 | 3/2001 |
| WO | 01/19268 A1 | 3/2001 |
| WO | 01/26566 | 4/2001 |
| WO | 01/54601 A1 | 8/2001 |
| WO | 01/89400 A2 | 11/2001 |
| WO | 02/71963 | 9/2002 |
| WO | 02/96309 A1 | 12/2002 |
| WO | 03/02856 | 1/2003 |
| WO | 03/22166 | 3/2003 |
| WO | 03/28567 | 4/2003 |
| WO | 03/57055 | 7/2003 |
| WO | 2004/043277 A1 | 5/2004 |
| WO | 2004/089233 A1 | 10/2004 |
| WO | 2004/107957 A2 | 12/2004 |
| WO | 2005/018472 A1 | 3/2005 |
| WO | 2005/044121 A1 | 5/2005 |
| WO | 2007/014279 A2 | 2/2007 |
| WO | 2007/108734 A1 | 9/2007 |
| WO | 2009/023666 A2 | 2/2009 |
| WO | 2009/058969 A1 | 5/2009 |
| WO | 2011/032140 A1 | 3/2011 |
| WO | 2012/112327 A2 | 8/2012 |
| WO | 2013/045713 A1 | 4/2013 |
| WO | 2017/048909 A1 | 3/2017 |

OTHER PUBLICATIONS

European Patent Application No. 12006615.4: Extended European Search Report dated Jan. 21, 2013, 7 pages.

Haas, N.P., et al., "LISS-Less Invasive Stabilization System—A New Internal Fixator for Distal Femur Fractures," OP J., vol. 13(3), pp. 340-344, Georg Thieme Verlag, Dec. 1997 (in English).

Gautier, E., et al., "Porosity and Remodelling of Plated Bone After Internal Fixation: Result of Stress Shielding of Vascular Damage?", Biomaterials and Biomechanics 1983, Elsevier Science Publishers B.V. 1984 ("Gautier").

Expert Report of John F. Witherspoon (w/o Exhibits A-C) in the Pennsylvania Action, dated Apr. 9, 2008; 36 pages.

European Patent Application No. 12006606.3: Extended European Search Report dated Jan. 21, 2013, 7 pages.

English translation of International Patent Application No. PCT/CH03/00577: International Search Report dated Apr. 28, 2004, 6 pages.

Dr. Turen's Aug. 15, 2008 deposition transcript in the Pennsylvania Action (Ex. 61).

Dr. Parsons Aug. 7, 2008 deposition transcript in the Pennsylvania Action (Ex. 58).

(56) References Cited

OTHER PUBLICATIONS

Dr. Marsh's Jul. 26, 2008 Deposition transcript in the Pennsylvania Action (Ex. 52).
Docket sheet for the Pennsylvania Action—2:03-cv-0084 (CDJ) (Ex. 4) filed Jan. 7, 2003.
Docket sheet for the California Action—3:07-cv-00309-L-AJB (Ex. 1) Filed Feb. 14, 2007.
Defendant's Motion for Leave to Amend Answer to Assert Allegations of Inequitable Conduct, Civil Action No. 03-0084 (E.D. Pa.), dated Aug. 7, 2007.
Declaration of Robert A. King in Support of their Motion for Partial Summary Judgment of Invalidity of Claims 10-12 of U.S. Pat. No. 6,623,486 (without exhibits), dated Sep. 10, 2008.
Declaration of J. Russell Parsons, Ph.D. in Support of Synthes Opposition to Smith & Nephew's Motion for Summary Judgement of Invalidity of the '744 patent (w/o Exhibits 1-4) dated Sep. 29, 2008; 15 pages.
Declaration of J. Russell Parsons, Ph.D. in Support of Synthes Opposition to Smith & Nephew's Motion for Partial Summary Judgment of Invalidity of Method Claims 10-12 of U.S. Pat. No. 6,623,486 (with Exhibits 1-4), dated Sep. 29, 2008 (Dkt. 160) (Ex. 68).
Declaration of J. Lawrence Marsh, M.D. dated Nov. 22, 2010.
Declaration of J. Lawrence Marsh, M.D. dated Jun. 25, 2010.
Declaration of J. Lawrence Marsh, M.D. dated Jun. 3, 2010.
Declaration of Dr. Seligson in Support of Smith & Nephew's Motion for Partial Summary 175 Judgment of Invalidity of Claims 10-12 of U.S. Pat. No. 6,623,486 dated Sep. 9, 2008 (with Exhibit 1, pp. 16-66 dated Sep. 10, 2008).
Declaration of Clifford H. Turen, M.D. in Support of Synthes' Opposition to Smith & Nephew's Motion for Partial Summary Judgment of Invalidity of Method Claims 10-12 of U.S. Pat. No. 6,623,486 (with Exhibits 1-4 ), dated Sep. 29, 2008.
Declaration of Charles E. Van Horn, Esq., in Support of Synthes Opposition to Smith & Nephew's Motion for Summary Judgement of Invalidity of the '744 patent (w/o Exhibits 1-6) dated Sep. 29, 2008; 12 pages.
Court Order denying Synthes' Motion for Reconsideration of Claim Construction for the '486 Patent in the Pennsylvania Action, dated Jun. 30, 2008.
Collins Instruments de Chirurgie, published 1935, as illustrated at http://www.litos.com/pages/winkelstabilitaet_e.html (Sep. 26, 2007) ("Collin Catalog") [SNI-0258552-556] (Ex. 20).
Claim Construction Order in Pennsylvania Action, dated Feb. 4, 2008.
Brief in Support of Defendants' Motion for Leave to Amend Answer to Assert Allegations of Inequitable Conduct, Civil Action No. 03-0084 (E..D. Pa.), dated Aug. 7, 2007.
Bone Plating System, U.S. Appl. No. 09/660,287.
Bone Fixation Method, U.S. Appl. No. 09/848,251.
Bolhofner, et al., The Results of Open Reduction and Internal Fixation of Distal Femur Fractures Using a Biologic (Indirect) Reduction Technique; Journal of Orthopedic Trauma, vol. 10, No. 6, pp. 372-377, Liooincort-Raven Publishers, Copyright 1996.
AO/ASIF Instruments and Implants, A Technical Manual, Springer-Verlag, 1994 (the "AO-ASIF Manual").
Answer to Amended Complaint and Counterclaims, Civil Action No. 03-0084 (E .. D. Pa), filed Dec. 5. 2006.
Amended Complaint for Patent Infringement, Civil Action No. 03-0084 (E.D. Pa.), filed Nov. 13, 2006.
Ace SymmetryTM, "Curves in All the Right Places", 1996, 3 pages.
Ace Symmetry, "Curves in All the Right Places", 1996, 3 pages.
Ace Symmetry Trademark Titanium Upper Extremity Plates, Ace Medical Company, 1996, 2 pages.
Ace Symmetry (Trademark), "Curves in All the Right Places", Titanium Upper Extremity Plates, Ace Medical Company, 1996, 6 pages.
Ace Symmetry (Trademark) Titanium Upper Extremity Plates, Ace Medical Company, 6 pages.

510(k) Summary for Synthes (USA)'s Distal Femur Plate (DFP) System (K982222), dated Jul. 29, 1998 (attached as Exhibit O to Amended Answer).
510(k) Summary for Synthes (USA)'s Anatomical Locking Plate System (K961413), dated Aug. 7, 1996 (attached as Exhibit Q to Amended Answer).
510(k) Summary for Synthes (USA)'s 2.4 mm Universal Locking Plate System (K961421 ), dated Jun. 26, 1996 (attached as Exhibit S to Amended Answer).
510(k) Disclosure K982732, Oct. 8, 1998 (Synthes) ("K982732") [SNI-0259741-744] (Ex. 39).
510(k) Disclosure K963798, Nov. 27, 1996 (Synthes) ("K963798") [SNI-0258398] (Ex. 38).
510(k) Disclosure K962616, Sep. 3, 1996 (Synthes) ("K962616") [SNI-0258397] (Ex. 37).
510(k) Disclosure K961421, Jun. 26, 1996 (Synthes) ("K961421") [SNI-0258396] (Ex. 36).
510(k) Disclosure K961413, Aug. 7, 1996 (Synthes) ("K961413") [SNI-0259751] (Ex. 35).
4.5 mm Cannulated Screw Technique Guide, published 1995 (Synthes) [SNI-0259703-714] (Ex. 21).
35 U.S.C. .sctn.282 Notice in the Pennsylvania Action, dated Oct. 10, 2008.
"VariAx TM Distal Radius Locking Plate System", Stryker R, Copyright 2009, 12 pages.
"The New Comprehensive Stryker R VariAx TM Distal Radius Locking Plate System", Copyright 2009, 20 pages.
"Multiple Offerings of Plates, Screws and Pegs", Small Bone Innovations, Inc., Dec. 2009, 3 pages.
"Less Invasive Stabilization System (LISS) Technique Guide," Synthes (USA) Copyright 2000 (attached as Exhibit K to Amended Answer).
"Cone Drive History and Double Enveloping Technology", http://conedrive.com/history/html., accessed Apr. 20, 2006, 9 pages.
Zimmer Advertisement, J. of Orthopaedic Trauma, vol. 12, No. 5, Jun./Jul. 1998.
Vattolo, M., Thesis, "The Effect of Grooves in Osteosynthesis Plates on the Restructuring of the Corticalis," Laboratory for Experimental Surgery, Swiss Research Institute, 1986 (original in German, translation to English attached with Certification).
Update, Titanium LC-DCP Condylar Buttress Plate, Jun. 15, 1995 (Synthes) ("The LC-DCP update").
Universelle Rekonstruktionsplatte URP 2.4-3.2 (UniRecon-Registered), Swiss Dent, 17, 1996, pp. 19-25.
The Titanium Distal Radius Plate Technique Guide, published by Synthes, 1997.
The Titanium Distal Radius Plate Technique Guide, (the "DRP Guide") published by Synthes in 1996.
The Locking Reconstruction Plate Technique Guide, published by Synthes, 1997.
The Distal Radius Plate Instrument and Implant Set Technique Guide, (Synthes) ("1999 Radius Plate Guide").
The Distal Radius Plate Instrument and Implant Set Technique Guide, (Synthes) ("1998 Radius Plate Guide").
The 1998 Schuhli Guide.
Technique Guide: 2.4 mm Variable Angle LCP Distal Radius System. Synthes, 2008, 43 pages.
Technique Guide, Less Invasive Stabilization (LISS), Oct. 2003.
Synthes' Supporting Memorandum for Reconsideration of Claim Construction (without supporting Declaration) in the Pennsylvania Action, dated Feb. 19, 2008.
Synthes' Summary Judgment Motion of No Invalidity Based on K982222 Summary including supporting memorandum, and declarations of A. Silversti and B. Liu (with supporting exhibits), dated Sep. 10, 2008.
Synthes' Responsive Claim Construction Brief (without exhibits) for the Pennsylvania Action, dated Apr. 20, 2007.
Synthes' Response to Smith & Nephew's Statement of Facts in Support of Smith & Nephew's Motion for Summary Judgment of Invalidity of the '744 patent; dated Sep. 29, 2008; 19 pages.
Synthes' Response to Motion for Leave to Amend Answer, Civil Action No. Mar. 0084 (E.D. Pa.), dated Aug. 9, 2007.

(56) References Cited

OTHER PUBLICATIONS

Synthes' Reply to Smith & Nephew's Opposition to Synthes Motion for Reconsideration of Claim Construction for the '486 patent in the Pennsylvania Action, dated Mar. 14, 2008.
Synthes' Opposition to Smith & Nephew's Motion for Summary Judgment of Invalidity of the '744 patent; dated Sep. 29, 2008; 22 pages.
Synthes' Opening Claim Construction Brief (without supporting declaration and attached exhibits but including Appendix A & B) for the Pennsylvania Action, dated Mar. 16, 2007 (Dkt. 54) (Ex. 5).
Synthes' 1996 Titanium Modular Hand System brochure (the "Hand System Brochure") [SNI-0290287-294] (Ex. 47).
Synthes Titanium Modular Hand System, 1996.
Synthes Opposition to Smith & Nephew's Motion for Summary Judgment of Invalidity of Claims 10-12 of the '486 Patent, dated Sep. 29, 2008 (Dkt. 159) (Ex. 67).
Synthes 1997 Catalog, published by Synthes, Mar. 1997; part 2, 261 pgs.
Synthes 1997 Catalog, published by Synthes, Mar. 1997; part 1, 200 pgs.
Sutter, F., et al., "Titanplasma-beschichtetes Hohlschrauben- und Rekonstructions-platten-System (THRP) zur Oberbriickung van Kieferdefekten," Chirurg No. 55, pp. 741-748, 1984 [SNI-0006164-171], and translation thereof [SNI-0006152-163] (Ex. 33).
Surgical Instruments Catalog, Collin & Co., 1935 (original in French, translation to English of pp. 392-397 attached with certification).
Supplemental Expert Report of Clifford H. Turen, M.D., May 2009 (with Exhibit 1), dated Aug. 8, 2008(Ex.60).
Supplement to Apr. 9, 2008 Expert Report of John F. Witherspoon (without exhibits), dated May 14, 2008 (Ex. 74).
Supplement to Apr. 9, 2008 Expert Report of J. Lawrence Marsh in the Pennsylvania Action (with Exhibit 1), dated May 14, 2008 (Ex. 46).
Summary of Safety and Effectiveness Information [510(k) Summary], K982222, Jul. 29, 1998.
Stryker, "VariAx Distal Radius: Locking Plate System", wwvv.osteosynthesis.stryker.com, 2006, 12 pages.
Stay Order in Pennsylvania Action, dated Jul. 13, 2009.
Smith and Nephew's Opposition to Synthes Motion for Summary Judgment of No Invalidity Based on K982222( including Opposition Memorandum, Statement of Undisputed Facts, K. Doyle Declaration with Exhibits A-F and R. King's Declaration with Exhibits A-D), dated Sep. 29, 2008( Dkt. 154) (Ex. 63).
Smith & Newphew Statement of Undisputed Facts in Support of its Motion for Summary Judgment of Invalidity of U.S. Pat. No. 7,128,744; dated Sep. 29, 2008; 8 pages.
*Smith & Nephew, Inc. v. Rea*, Federal Circuit Opinion dated Jul. 9, 2013, 18 pages.
Smith & Nephew's Third Supplemental Response to Interrogatories Nos. 4, 5, 6, 8 and 9; Second Supplemental Responses to Interrogatories Nos. 1, 2, 3, 10, 11 and 12; and First Supplemental Responses to Interrogatories Nos. 13, 15 and 17 (with Smith & Nephew Exhibit 1 thereto), dated Aug. 11, 2008 (Ex. 14).
Smith & Nephew's Responsive Claim Construction Brief (without exhibits) for the Pennsylvania Action, dated Apr. 20, 2007 (Dkt. 60) (Ex. 8).
Smith & Nephew's Responses and Objections to Plaintiffs Fourth Set of Interrogatories Nos. 15-16, dated May 21, 2008 (Ex. 55).
Smith & Nephew's Opposition to Synthes' Motion for Reconsideration of Claim Construction for the '486 Patent in the Pennsylvania Action, dated Mar. 4, 2008 (Dkt. 108) (Ex. 11).
Smith & Nephew's Opening Claim Construction Brief (without exhibits) for the Pennsylvania Action, dated Mar. 16, 2007 (Dkt. 53) (Ex. 6).
Smith & Nephew's Memorandum in Support of Motion for Leave to file Amended Answer in the Pennsylvania Action, dated Aug. 7, 2007 (Dkt. 77) (Ex. 70).
Smith & Nephew's Memorandum in Support of its Motion for Summary Judgment of Invalidly of U.S. Pat. No. 7,128,744; dated Sep. 10, 2008; 22 pages.
Smith & Nephew's Memorandum in Support of its Motion for Partial Summary Judgment of Invalidity of Claims 10-12 of the '486 patent, dated Sep. 10, 2008.
Smith & Nephew's Amended Answer in the Pennsylvania Action (without Exhibits A-S ) in the Pennsylvania Action, dated Aug. 7, 2007.
Smith & Nephew Amended Answer and Counterclaims of Defendant, Civil Action No. 03-0084 (E.D. Pa.), dated Aug. 7, 2007.
Second Supplement to Apr. 9, 2008 Expert Report of J. Lawrence Marsh (with Exhibit 1), dated Sep. 3, 2008.
Second Supplement to Apr. 9, 2008 Expert Report of David Seligson, M.D., dated Sep. 3, 2008.
Schuhli Technique Guide, published by Synthes, 1995.
Schuhli Technique Guide 1998, (Synthes) ("Schuhli Guide").
Schmoker, The Locking Reconstruction Plate 2.4-3.2, originally published in Swiss Dent 17, 1996.
Schandelmaier, et al., Distal Femur Fractures and LISS Stabilization, Injury, Int. J. Care Injured, vol. 32, Suppl. 3, 55-63, 2001.
Ring, D., et al. "Prospective Multicenter Trial of a Plate for Distal Fixation of Distal Radius Fractures," J. of Hand Surgery, vol. 22a(5), pp. 777-784, Sep. 1997.
Ring, D., et al,"A New Plate for Internal Fixation of the Distal Radius," AO.ASIF Dialogue, vol. IX, issue I, Jun. 1996 [SNI-0254971-973] (Ex. 53).
Reply to Counterclaims, Civil Action No. 03-0084 (E.D. Pa.). filed Jan. 2, 2007.
Rebuttal Expert Report of Russell Parsons, Ph.D., (with Exhibit 1), dated Jul. 15, 2008.
Rebuttal Expert Report of Mari Truman, P.E., (with Exhibit 2), dated May 14, 2008 (Ex. 79).
Rebuttal Expert Report of Eric R. Gozna, M.D., P.ENG., (with Exhibit 1), dated May 13, 2008 (Ex. 56).
Rebuttal Expert Report of Clifford H. Turen, M.D., (with Exhibit 1 ), dated May 14, 2008.
Rebuttal Expert Report of Charles E. Van Horn (without Exhibits), dated May 12, 2008 (Ex. 77).
Pure Titanium Implants Catalog, published Dec. 1993 (Synthes) ("PTI") [SNI0259670-673] (Ex. 23).
Printout of http://www.aofoundation.org web site, dated May 23, 2007 (attached as Exhibit L to Amended Answer).
Printout from USFDA 510(k) Premarket Notification Database, dated May 23, 2007, listing Synthes Distal Femur Plate (DFP) System, and bearing 510(k) No. K982222 (attached as Exhibit N to Amended Answer.
Printout from US FDA 510(k) Premarket Notification Database, dated May 22, 2007, listing Synthes Anatomical Locking Plate System, and bearing 510(k) No. K961413 (attached as Exhibit P to Amended Answer).
Photographs of the Pi plate marked as Little Deposition Exhibit 84.
Photographs of the Bolhofner Distal Femur Plating System (Bolhofner DFPS), Apr. 14, 2008.
Photographs of Synthes Titanium Distal Femur LISS Plate, 9 holes/236 mm—Right, 42.344 (the sample LISS)(SYN-PHY-0000002).
Photographs of Synthes Less Invasive Stabilization System (LISS), screw; (SYN-PHY0000004).
Photographs of Sample Synthes LC-DCP Tibia Plate produced as SYN-PHY-0000014.
Photographs of Sample Synthes LC-DCP CBP produced as SYN-PHY-0000011.
Photographs of sample LC-DCP Condylar Buttress Plate ("CBP") [SYN-PHY-0000001] (Ex. 42).
Perren, S., et al., "Early Temporary Porosis of Bone Induced by Internal Fixation Implants," Clinical Orthopaedics and Related Research, No. 232, Jul. 1988, 139-151.
Perren, et al., "The Limited Contact Dynamic Compression Plate (LC-DCP)," Arch. Orthopaedic & Trauma Surg., 1990, vol. 109, 304-310.
Ms. Truman's Jul. 24, 2008 deposition transcript in the Pennsylvania Action (Ex. 81).
Mr. Van Horn's Jul. 15, 2008 deposition transcript in the Pennsylvania Action (Ex. 78).

(56) References Cited

OTHER PUBLICATIONS

Marsh Exhibit C, Declaration of J. Lawrence Marsh, MD., in support of Smith & Nephew's, Inc's Motion for Partial Summary Judgement of Invalidity of Claims 10-12 of U.S. Pat. No. 6,623,486, dated Sep. 9, 2008, pp. 1-20.
Marsh Exhibit B, Supplement to Apr. 9, 2008 Expert Report of J. Lawrence Marsh, MD, Civil Action No. 03-0084, dated May 14, 2008 , pp. 1-19.
Marsh Exhibit A, Releasable 510(k) Search, Aug. 7, 2000, http://web.archive.org/web/19970615015534/www.fda.gov/egibin/htmlscript?5-IOk.hts+showcat-OR.
Marsh Exhibit A, Initial Expert Report of J. Lawrence Marsh, MD, Civil Action No. 03-0084, dated Apr. 9 , 2008 , pp. 1-181.
Marsh Exhibit A dated Jun. 25, 2010.
Marsh Exhibit 1, Curriculum Vitae, Dec. 2006, pp. 1-34.
Marsh Exhibit 1, Affidavit of Christopher Butler dated Aug. 24, 2010.
Marsh Exhibit 1 dated Nov. 22, 2010.
Marsh Exhibit 1 dated Jun. 25, 2010.
Manual of Internal Fixation, Techniques Recommended by the AO-ASIG Group, Springer-Verlag, 1991, 200-251.
Luthi, U., et al., "Kontackflache zwischen Osteosyntheseplatte and Knochen," Aktuel. Traumatol. 10:131-136, 1980 ("Luthi") [SNI-0258572-577] (Ex. 31).
Less Invasive Stabilization System LISS Surgical Technique Proximal Tibia, (Draft), 2000, 11 pgs.
Krettek, C., LISS: Less Invasive Stabilization System, AO Dialogue, vol. 12(1), Jun. 1999 ("Krettek").
Krettek et al.; "Distale Femurfrakturen"; Swiss Surg.; 1998; 4; p. 263-278 (no English Translation).
Krettek et al, "LISS less Invasive Stabilization System," AO International Dialogue, vol. 12, Issue I, Jun. 1999.
Koval, k., et al., "Distal Femoral Fixation: A Biomechanical Comparison of the Standard Condylar Buttress Plate, a Locked Buttress Plate, and the 95-Degree Blade Plate," J. of Orthopaedic Trauma, val. 11(7), pp. 521-524, Lippencott-Raven Publishers, Oct. 1997.
Kolodziej, P., et al. "Biomechanical Evaluation of the Schuhli Nut," Clinical Orthopaedics and Related Research, No. 34 7, pp. 79-85, Lippencott-Raven Publishers, Feb. 1988 ("Kolodziej") [SNI-0256042-048] (Ex. 28).
Kassab, et al., "Patients Treated for Nonunions with Plate and Screw Fixation and Adjunctive Locking Nuts," Clinical Orthopaedics and Related Research, 1998, 347, 86-92.
Joint submission setting forth agreed claim construction in the Pennsylvania Action, dated Jul. 31, 2007.
International Search Report for International Application No. PCT/CH03/00577, dated Apr. 28, 2004, English language translation of the German language version.
International Patent Application No. PCT/US2008/072894: International Search Report dated Mar. 19, 2009, 18 pages.
Initial Expert Report of J. Lawrence Marsh, M.D., Apr. 9, 2008 (with Exhibits 1-2 and Appendices A-L), dated Apr. 9, 2008 (Ex. 41).
Initials Disclosures of Defendant, Civil Action No. 03-0084 (E.D. Pa), dated Jan. 12, 2007.
Information Disclosure Statement in U.S. Appl. No. 09/660,287, dated Nov. 13, 2000 (attached as Exhibit G to Amended Answer).
Information Disclosure Statement bearing, dated May 4, 2001 (attached as Exhibit F to Amended Answer).
U.S. Appl. No. 15/926,390, Bone Plate With Form-Fitting Variable-Angle Locking Hole, filed Mar. 20, 2018.

\* cited by examiner

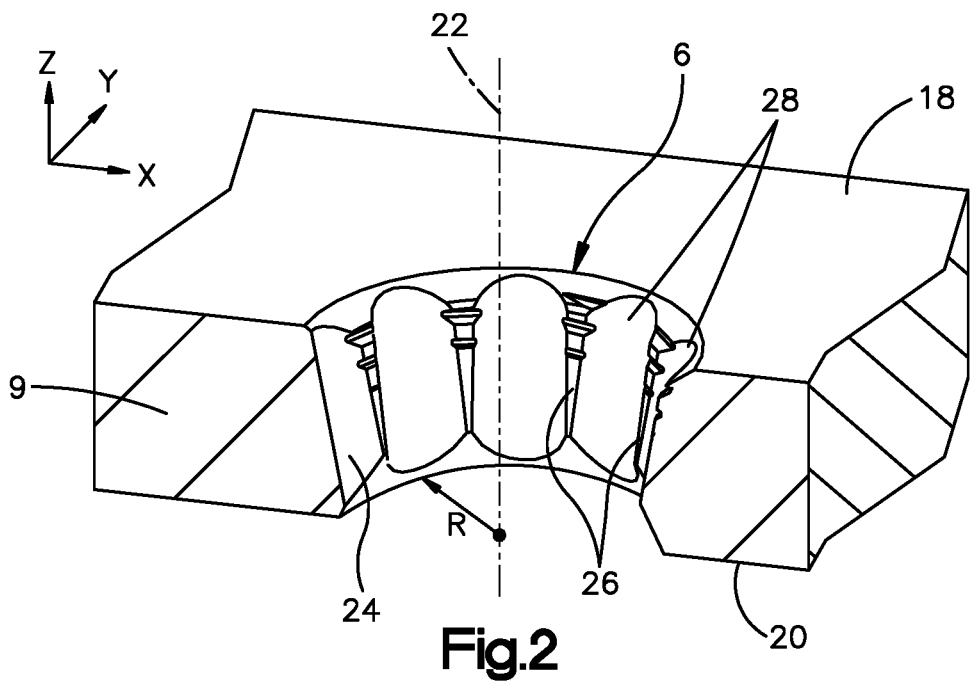
Fig.2
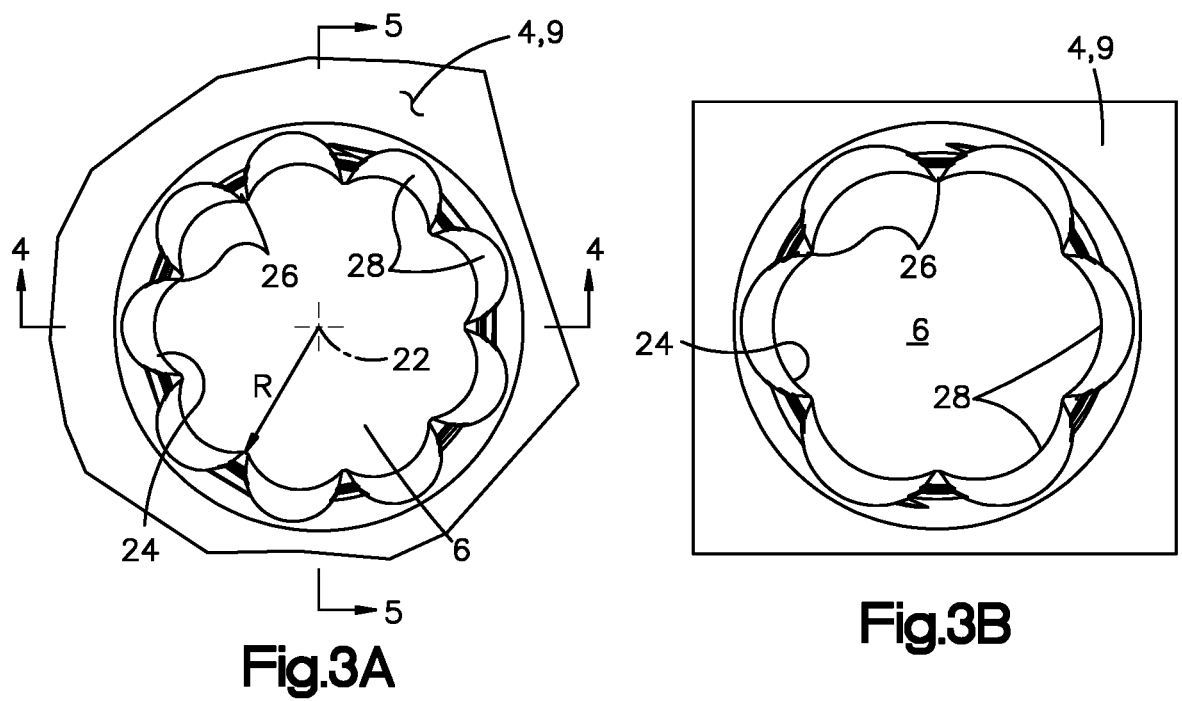
Fig.3A
Fig.3B

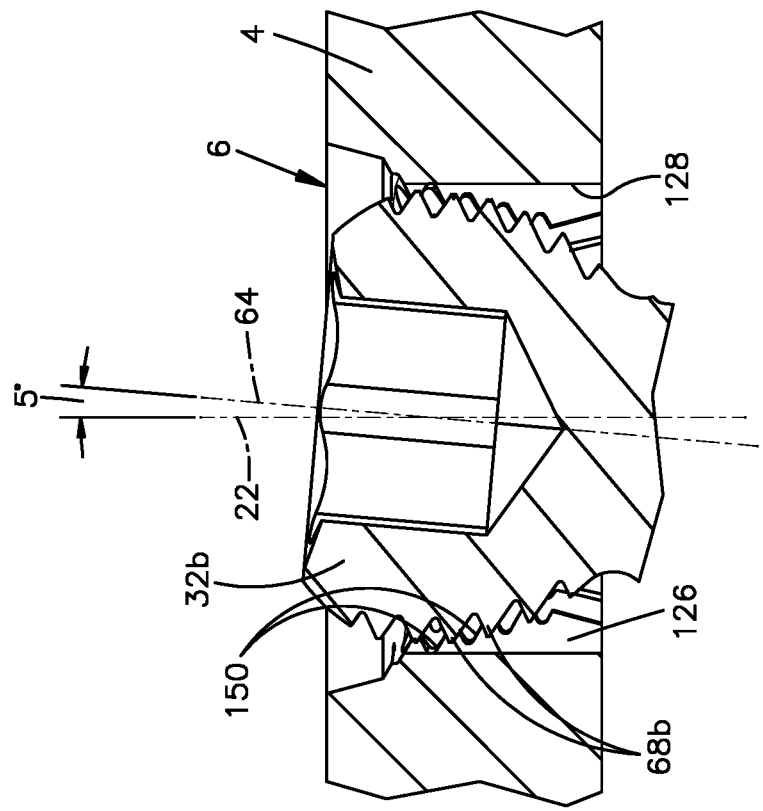
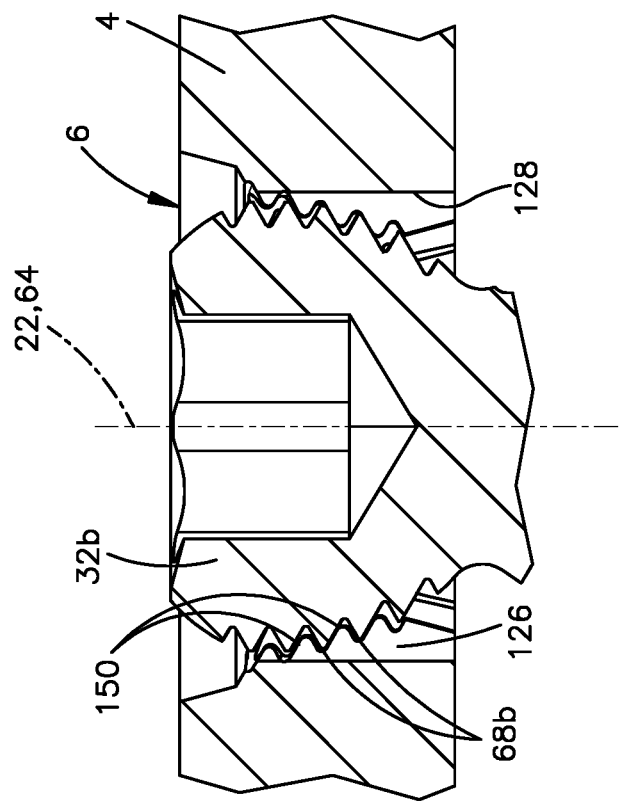

LOCKING STRUCTURES FOR AFFIXING BONE ANCHORS TO A BONE PLATE, AND RELATED SYSTEMS AND METHODS

CROSS REFERENCE TO RELATED APPLICATIONS

This application is related to U.S. patent application Ser. No. 15/926,390, filed on Mar. 20, 2018, in the name of Bosshard, et al., the disclosure of which is hereby incorporated by reference as if set forth in its entirety herein.

TECHNICAL FIELD

The present invention relates to bone plates and bone anchors for coupling to the bone plates, and particularly relates to locking structures defined within an aperture of a bone plate for locking with a head of a bone anchor.

BACKGROUND

Bone plate systems for the internal fixation of bone fractures are well known. Conventional bone plate systems are particularly well-suited to promote the healing of a fracture. A bone anchor, such as a bone screw, is inserted through a bone plate aperture or hole and is threaded into bone to compress, neutralize, buttress, tension bend, and/or bridge the fracture ends together. To transfer loads from one fractured bone part, over a plate, and onto another fractured bone part without drawing the bone against the plate, and to avoid loosening or backing out the bone screws with respect to the plate (which can lead to poor alignment and poor clinical results), bone screws that are capable of locking with the bone plate can be employed. One known embodiment of such a screw employs a screw head with external threads for engaging with a corresponding thread on the inner surface of a bone plate aperture to lock the screw to the plate. These screws (which are hereinafter referred to as "locking screws" or "locking compression screws"), which can include standard-type locking screws that are configured to lock within an aperture substantially only at a "nominal" orientation whereby the central screw axis is substantially aligned with the central aperture axis, as well as "variable-angle" (VA) locking screws, which are configured to lock within an aperture at either a nominal orientation or an "angulated" orientation whereby the central screw axis is oriented at an acute angle with respect to the respective central aperture axis.

SUMMARY

According to an embodiment of the present disclosure, a bone plate includes an upper surface configured to face away from a bone, an opposed lower surface configured to face the bone, and at least one aperture extending through the bone plate from the upper surface to the lower surface along a central aperture axis. The at least one aperture is defined by an interior surface of the bone plate. The interior surface further defines a plurality of columns sequentially located about a circumference of the interior surface and a plurality of recesses located circumferentially between the columns. Each of the columns is configured to undergo deformation at least in a radial direction perpendicular to the central aperture axis responsive to engagement with a head of a locking bone screw that is receivable within the at least one aperture so as to lock the head to the bone plate. The plurality of columns comprises at least five columns.

BRIEF DESCRIPTION OF THE DRAWINGS

The foregoing summary, as well as the following detailed description of illustrative embodiments of the present application, will be better understood when read in conjunction with the appended drawings. For the purposes of illustrating the locking structures of the present application, there is shown in the drawings illustrative embodiments. It should be understood, however, that the application is not limited to the precise arrangements and instrumentalities shown. In the drawings:

FIG. 2 is a sectional perspective view of an aperture of the bone plate shown in FIG. 1;

FIG. 3A is a top plan view of the aperture shown in FIG. 2;

FIG. 3B is a top plan view of an aperture, according to another embodiment of the present disclosure;

FIG. 17 is a section view of a variable-angle locking screw locked within the aperture of FIG. 16 at a nominal orientation;

FIG. 18 is a section view of the variable-angle locking screw locked within the aperture of FIG. 16 at an angulation of about 5 degrees;

DETAILED DESCRIPTION OF ILLUSTRATIVE EMBODIMENTS

The present disclosure can be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the scope of the present disclosure. Also, as used in the specification including the appended claims, the singular forms "a," "an," and "the" include the plural, and reference to a particular numerical value includes at least that particular value, unless the context clearly dictates otherwise.

The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

VA locking screws have a tendency to cause cross-threading within an aperture of a bone plate in which they are inserted. Cross-threading can be caused by the external threads on the screw head not fitting within and thus cross-threading the internal threading of the aperture. Cross-threading is problematic because it reduces the interference fit (also referred to as the "form-fit") between the internal threading of the aperture and the screw head threads, which can result in a reduction of stability between the screw head and the aperture of the bone plate. The embodiments disclosed herein pertain to locking structures employed within the apertures of a bone plate, which structures are configured to lock with the heads of both standard-type and VA locking screws in a manner inhibiting or at least reducing cross-threading.

Figure 1:
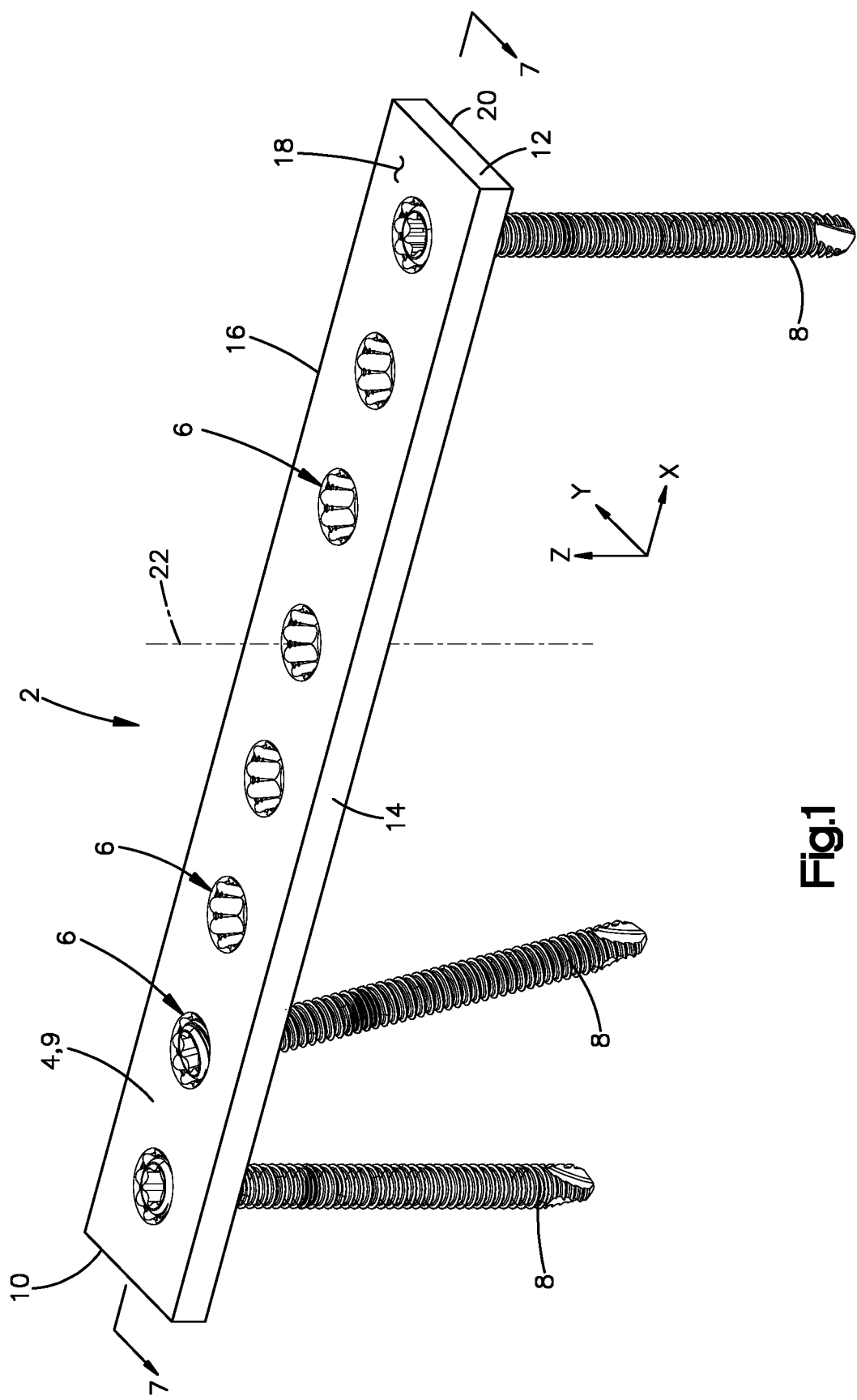
FIG. 1 is a perspective view of a bone fixation system including a bone plate defining apertures with locking screws received therein, according to an embodiment of the present disclosure.

Referring to FIG. 1, a bone fixation system 2 includes a bone plate 4 having one or more apertures 6 defined therein. The apertures 6 are configured to receive anchor members, such as locking screws 8, for example, that are configured to affix the bone plate 4 to one or more portions of bone. The apertures 6 have locking structures therein that are configured to deform around the heads of the locking screws 8 in a manner providing enhanced locking engagement between the locking screws 8 and the bone plate 4, as set forth in more detail below. The bone plate 4 can be a bridge plate, as shown, although other bone plate types and configurations are within the scope of the present disclosure.

The bone plate 4 can include a body 9 that defines a first end 10 and a second end 12 spaced from each other along a longitudinal direction X and a first lateral side 14 and a second lateral side 16 spaced from each other along a lateral direction Y that is substantially perpendicular to the longitudinal direction X. The bone plate 4 can also define an upper plate surface 18 configured to face away from the bone and an opposed lower plate surface 20 configured to face the bone. The upper and lower plate surfaces 18, 20 are spaced from each other along a vertical direction Z substantially perpendicular to each of the longitudinal direction X and the lateral direction Y.

It is to be appreciated that, as used herein, the terms "longitudinal", "longitudinally", and derivatives thereof refer to the longitudinal direction X; the terms "lateral", "laterally", and derivatives thereof refer to the lateral direction Y; and the terms "vertical", "vertically", and derivatives thereof refer to the vertical direction Z.

The plate body 9 and the locking screws 8 can each comprise one or more biocompatible materials, such as titanium, titanium alloys (e.g., titanium-aluminum-niobium (TAN) alloys, such as Ti-6Al-7Nb), stainless steel, cobalt base alloys, composite materials, and polymeric materials and/or ceramic materials, by way of non-limiting examples. Preferably, the screw 8 material is harder than the plate body 9 material, which provides for beneficial locking characteristics between the locking screws 8 and the bone plate 4, as described in more detail below. In one example embodiment, the plate body 9 primarily or entirely comprises titanium and the locking screws 8 primarily or entirely comprise TAN.

Referring now to FIG. 2, the apertures 6 extend vertically from the upper plate surface 18 to the lower plate surface 20 along a central aperture axis 22. In the depicted embodiment, the central aperture axis 22 is oriented along the vertical direction Z, although in other embodiments the central aperture axis 22 can be offset and angulated from the vertical direction Z. Each of the apertures 6 can be defined by an interior surface 24 of the plate body 9. Within the apertures 6, the interior surface 24 can define a plurality of locking structures, such as columns 26, that are configured to deform around the head of a locking screw 8 in a manner locking the screw head in position within the aperture 6.

Within each (or at least some of) the apertures 6, the columns 26 are sequentially located about a circumference of the interior surface 24 so as to define a plurality of recesses 28 sequentially located circumferentially between the columns 26. The columns 26 extend vertically between the upper and lower plate surfaces 18, 20 and are configured to deform at least in a radial direction R that is oriented perpendicular to the central aperture axis 22 responsive to engagement with an outer surface of a head of one of the locking screws 8. In this manner, the radial deformation of one or more of the columns 26 provides a form-fit and a compression fit (i.e., a "press-fit") between the plate body 9 and the screw head within the aperture 6, which form-fit and press-fit preferably locks the head (and thus the screw 8) to the plate body 9 at a fixed orientation, as described in more detail below. It is to be appreciated that, as used herein, the terms "radial", "radially", and derivatives thereof refer to the radial direction R.

Referring now to FIG. 3A, the columns 26 and recesses 28 can be evenly spaced about the circumference of the interior surface 24 within the aperture 6. However, in other embodiments, the columns 26 and/or recesses 28 can be un-evenly spaced about the circumference of the aperture 6. As depicted in FIG. 3A, the aperture 6 can include nine (9) columns 26, although fewer than nine (9) columns 26 or more than nine (9) columns 26 can be employed in the aperture 6. For example, each aperture 6 can include five (5) or fewer columns 26, six (6) columns 26, seven (7) columns 26, eight (8) columns 26, or ten (10) or more columns 26. For example, FIG. 3B shows an embodiment of an aperture 26 with six (6) columns 26. In further embodiments, each aperture 6 can include between ten (10) and twenty (20) columns 26 or more than twenty (20) columns 26.

Figure 4:
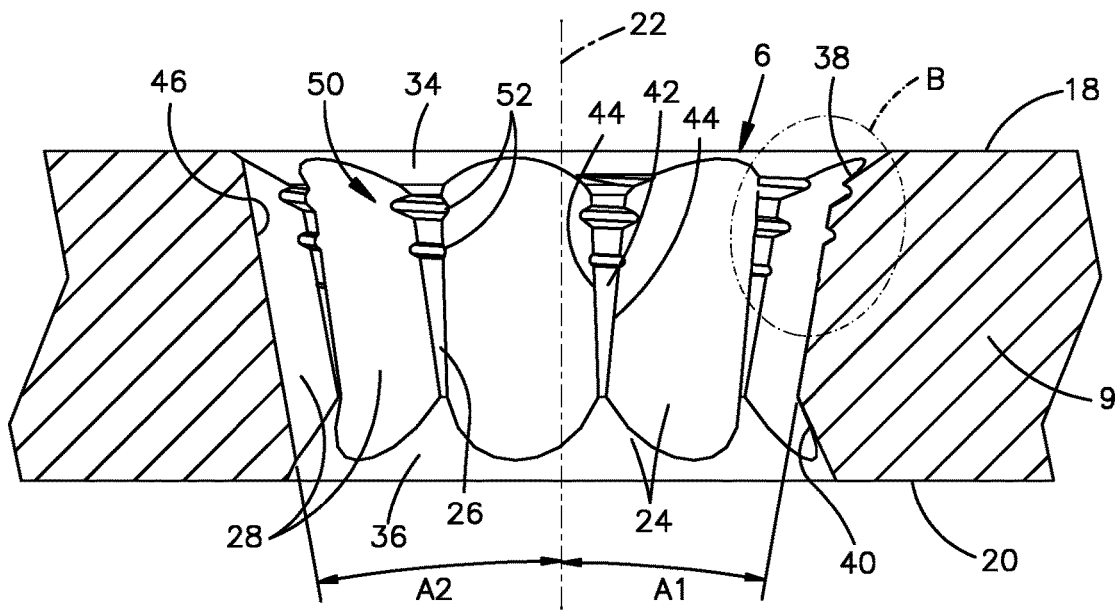
FIG. 4 is a sectional side view of the aperture taken along section line 4-4 in FIG. 3A.
Figure 5:
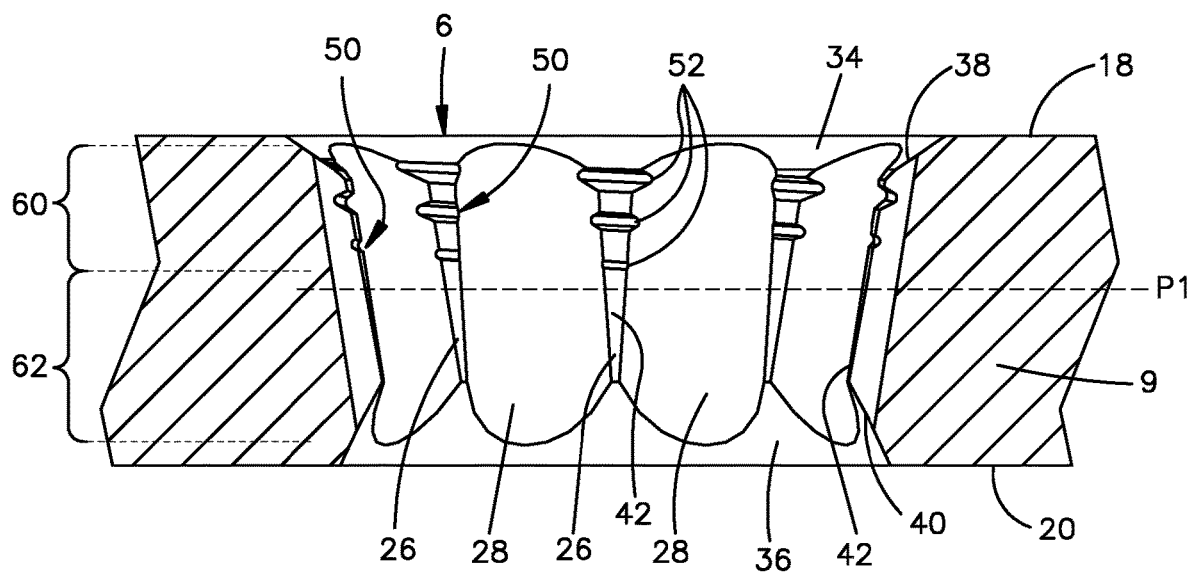
FIG. 5 is a sectional side view of the aperture taken along section line 5-5 in FIG. 3A.

Referring now to FIGS. 4 and 5, the interior surface 24 can include an upper relief surface 34 extending from the upper plate surface 18 toward the lower plate surface 20 and a lower relief surface 36 extending from the lower plate surface 20 toward the upper plate surface 18. The lower relief surface 36 and the upper relief surface 34 can each define a respective relief angle in a range of about 1 degree to about 60 degrees from the central aperture axis 22. In the illustrated embodiment, the relief angle of the lower relief surface 36 is about 15 degrees and the relief angle of the upper relief surface 34 is about 45 degrees. The upper relief surface 34 can define an upper end 38 of the columns 26 and the lower relief surface 36 can define a lower end 40 of the columns 26. The upper relief surface 34 can be configured to accommodate (i.e., house or provide space for) an angulated screw head, and the lower relief surface 36 can be configured to accommodate the shaft of an angulated screw 8.

Each column 26 can define a first surface 42 substantially facing the central aperture axis 22, and a pair of side surfaces 44 located on adjacent circumferential sides of the first surface 42. The first surface 42 can also be referred to as an "innermost surface" of the column 26. Each side surface 44 of the column 26 can define at least a portion of the circumferentially adjacent recess 28. Each recess 28 can extend from the first surface 42 of one adjacent column 26 to the first surface 42 of the other adjacent column 26. The recesses 28 can extend continuously in a circumferentially arcuate manner between adjacent columns 26, although other recess configurations are within the scope of the present disclosure.

Within one or more of the apertures 6, the first surfaces 42 of the columns 26 can collectively define segments of a first shape, such as a first inverted frusto-conical shape. The nadirs 46 (i.e., the lowest point) of the recesses 28 can collectively define segments of a second shape, such as a second inverted frusto-conical shape that is wider than the first inverted frusto-conical shape. In the illustrated embodiments, the first and second inverted frusto-conical shapes have a common cone angle, although in other embodiments the first and second inverse cone shapes can have different cone angles. In yet other embodiments, the first and second shapes can be circular, elliptical, parabolic, or other types of geometries.

In the illustrated embodiment, the first inverse cone shape causes each first surface 42 within the aperture 6 to have a concave profile in a horizontal reference plane P1 (i.e., a plane extending along the longitudinal and lateral directions X, Y). It is to be appreciated, however, that in other embodiments, the first surfaces 42 within an aperture 6 can be convex in the horizontal reference plane P1. In such embodiments, the apices of the first surfaces 42 of the columns 26 can collectively define the first inverted cone shape. In yet other embodiments, the first surfaces 42 within an aperture 6 can have a linear profile in the horizontal reference plane P1.

Referring again to the illustrated embodiment, the interior surfaces 24 of the apertures 6 can initially be formed to define an inverted cone shape with a tool, such as a conical drill bit and/or milling cutter, by way of non-limiting examples. The recesses 28 can be subsequently formed, such as with a milling cutter that removes plate body 9 material sequentially about the circumference of the aperture 6 so as to form the recesses 28 and the distinct columns 26 therebetween. The upper and lower relief surfaces 34, 36 can be formed with one or more angle or dovetail mills, by way of non-limiting example.

With continued reference to FIGS. 4 and 5, the first surfaces 42 of each of the columns 26 within an aperture 6 can taper radially inwardly from the upper plate surface 18 to the lower plate surface 20 at a first angle A1 in a range of about 3 degrees to about 30 degrees relative to the central aperture axis 22, and preferably in a range of about 10 degrees to about 15 degrees relative to the central aperture axis 22. Additionally, the nadirs 46 of the recesses 28 within an aperture 6 can taper radially inwardly from the upper plate surface 18 to the lower plate surface 20 at a second angle A2 in a range of about 3 degrees to about 30 degrees relative to the central aperture axis 22, and preferably in a range of about 10 degrees to about 15 degrees relative to the central aperture axis 22. The radius of each recess 28 can be the same at any vertical location within the recess 28; although in other embodiments the radius of each recess 28 can vary. Additionally, as shown, the first surfaces 42 of the columns 26 can increase in circumferential width moving vertically from the lower plate surface 20 toward the upper plate surface 18 (and thus decrease in circumferential width moving vertically from the upper plate surface 18 toward the lower plate surface 20). As depicted, the first and second angles A1, A2 can be substantially equivalent, although in other embodiments they can be offset.

One or more of the apertures 6 can include internal threading 50 for engaging external threads on the outer surface of a screw head. The internal threading 50 preferably helically traverses each column 26 in the aperture 6 such that each column 26 defines one or more thread portions 52 of the internal threading 50. The threading 50 can be configured to terminate between the upper and lower ends 38, 40 of the columns 26. In this manner, each column 26 can define an upper column portion 60 encompassing the one or more thread portions 52 and a lower column portion 62 devoid of the internal threading 50. Stated differently, the lower column portions 62 can have no threading, at least prior to engagement with the head of a locking screw 8.

Figure 6:
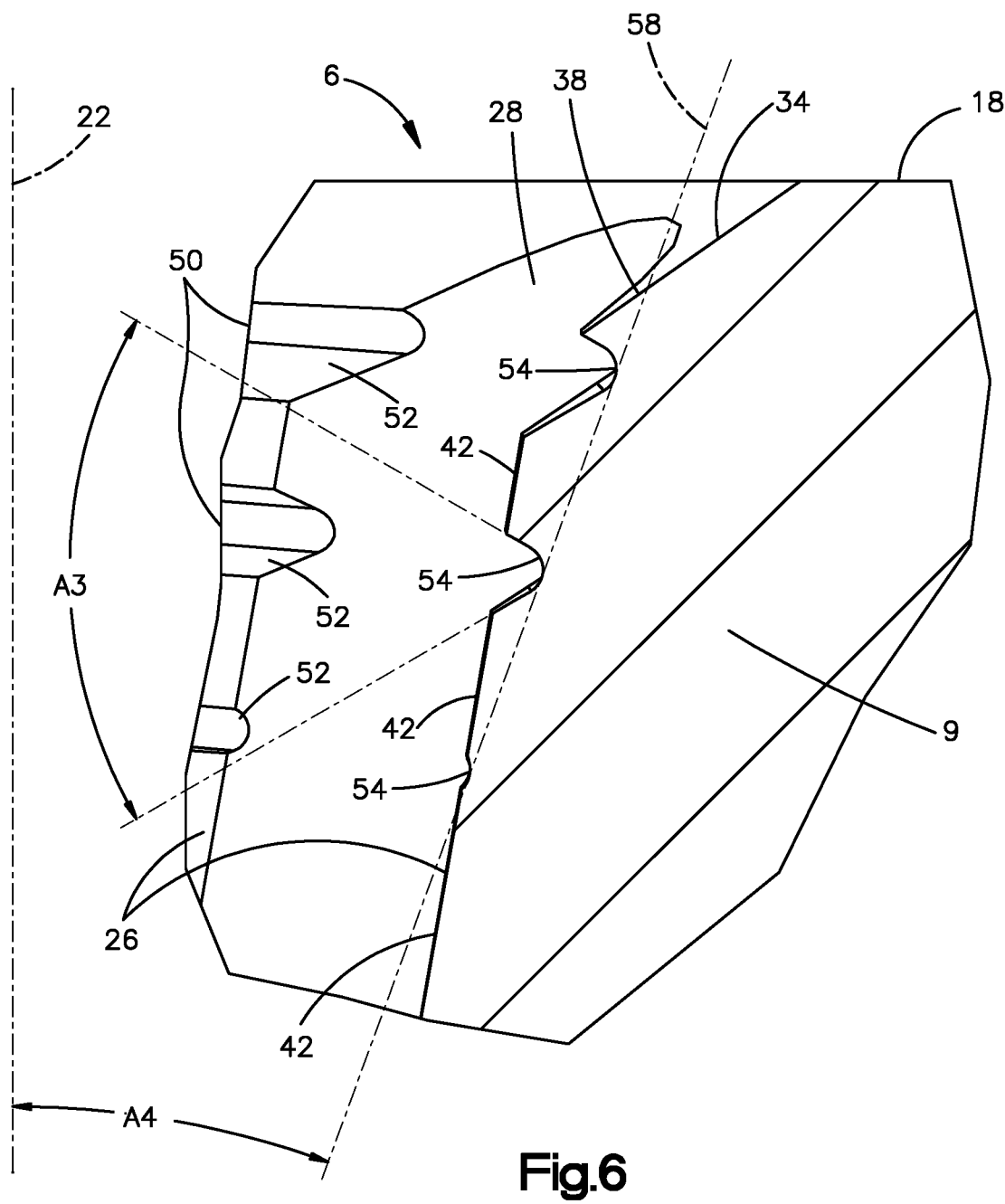
FIG. 6 is a sectional side view of enlarged portion B of the aperture shown in FIG. 4.

Referring now to FIG. 6, the thread portions 52 can include a thread root 54 recessed radially outward from the first surface 42 of the respective column 26. The thread portions 52 of the columns 26 can define a third or thread angle A3 in a range of about 30 degrees to about 90 degrees, preferably in the range of about 55 degrees to about 65 degrees, and more preferably at about 60 degrees. The thread portions 52 can define a thread pitch in a range of about 0.1 mm to about 1.6 mm, and more preferably at about 0.8 mm, by way of non-limiting examples. The threading 50 is preferably a right-hand thread, although left-hand threading 50 is within the scope of the present disclosure. The threading 50 can be dual-lead, as shown, although single-lead or triple-lead threading 50 is also within the scope of the present disclosure.

In the present embodiment, the one or more thread portions 52 of each column 26 is tapered along a threading profile 58 that extends substantially linearly along the roots 54 and is oriented such that the threading profile 58 and the central aperture axis 22 are each coextensive in a common vertical reference plane. The threading profile 58 can be angled radially inwardly from the upper plate surface 18 to the lower plate surface 20 at a fourth angle A4 or "threading slope" in a range of about 4 degrees to about 40 degrees relative to the central aperture axis 22, and preferably in a range of about 11 degrees to about 30 degrees relative to the central aperture axis 22, and more preferably at about 20 degrees relative to the central aperture axis 22. The fourth angle A4 can be referred to as the "internal threading slope." In the present embodiment, the threading slope A4 preferably exceeds the first angle A1, causing the internal threading 50 to terminate at a location between the upper and lower ends 38, 40 of the columns 26, as described above.

Figure 7:
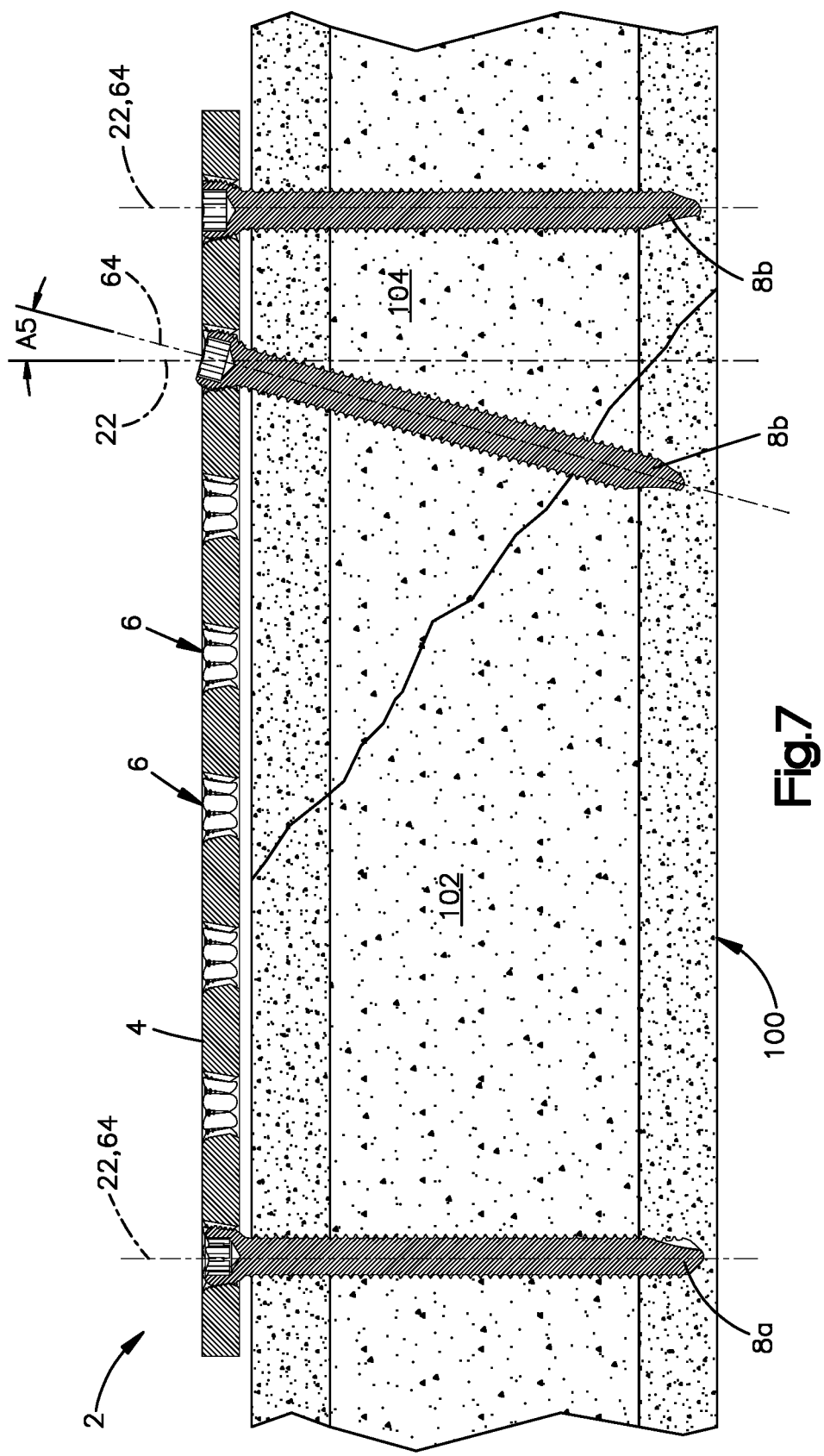
FIG. 7 is a sectional side view of the bone fixation system taken along section line 7-7 in FIG. 1.

Referring now to FIG. 7, the apertures 6 can be configured to provide enhanced affixation with multiple types of locking screws 8, including standard-type locking screws 8a and VA locking screws 8b, so as to allow a physician to implant the bone plate 4 to one or more bones or bone segments as desired. As shown, the bone plate 4 can be coupled to a long-bone 100 via locking screws 8a, 8b in a manner affixing fractured segments 102, 104 of the bone together. The apertures 6 described herein can lock with standard-type locking screws 8a at a nominal orientation whereby the central screw axis 64 is substantially aligned with the central aperture axis 22, as well as VA locking screws 8b at either a nominal orientation or an "angulated" orientation whereby the central screw axis 64 is oriented at an acute angle A5 with respect to the respective central aperture axis 22. The acute angle A5 can also be referred to as the "angle of angulation" or simply the "angulation." Both types of locking screws 8a, 8b and their locking functionalities are described more fully in U.S. Pat. No. 9,314,284, issued Apr. 19, 2016, in the name of Chan et al. (the "Chan Reference"), the entire disclosure of which is incorporated by reference herein.

With reference to FIGS. 8 through 12, engagement between the columns 26 and standard-type locking screws 8a (FIGS. 8 and 9) and VA locking screws 8b (FIGS. 10 through 12) will now be described.

Figure 8:
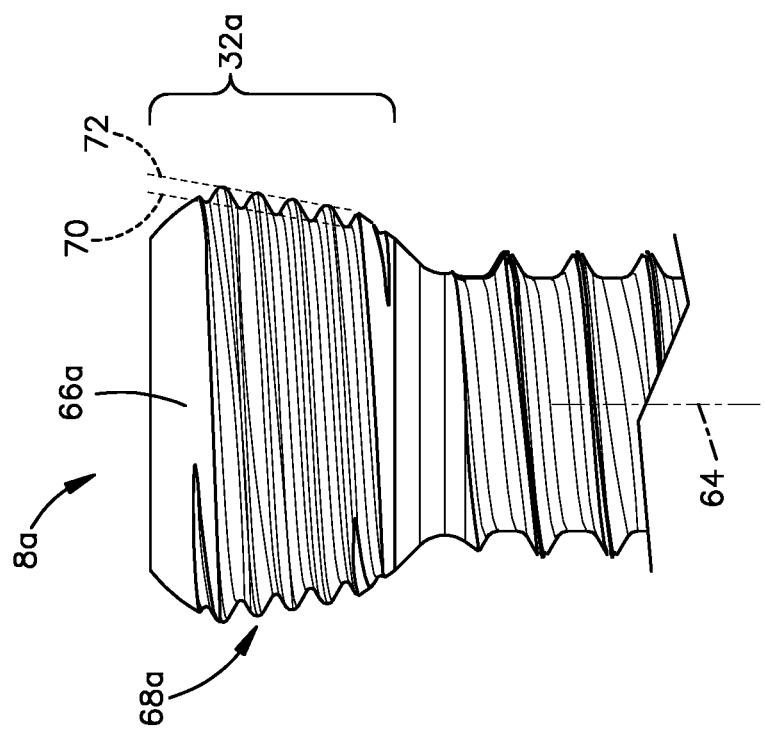
FIG. 8 is a side view of the head portion of a standard-type locking screw configured to be locked within an aperture of a bone plate at a nominal orientation.

Referring now to FIG. 8, a standard-type locking screw 8a can have a screw head 32a defining a conical outer surface 66a defining external screw head threads 68a. The external screw head threads 68a have a first threading profile 70 measured at the thread roots and a second threading profile 72 measured at the thread crests. As depicted, the standard-type locking screw 8a has conical first and second threading profiles 70, 72 that are parallel; additionally the profiles 70, 72 taper downwardly so as to provide the screw head 32a with a locking functionality as the screw head 32 advances within the aperture 6.

Figure 9:
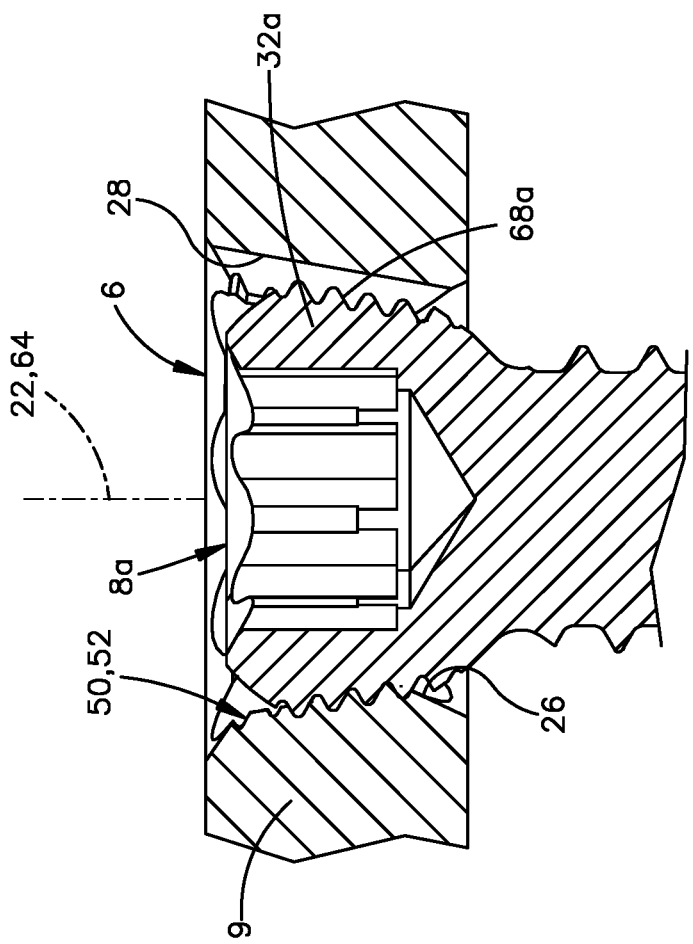
FIG. 9 is a sectional side view of the head of the standard-type locking screw of FIG. 8 locked within an aperture of the bone plate of FIG. 7.

Referring now to FIG. 9, the internal threading 50 of the aperture 6 is configured to engage the external screw head threads 68a in an interconnecting manner so as to substantially induce a form-fit interaction therebetween (i.e., the apices of the external screw head threads 68a extend within the troughs of the internal threading 50 of the aperture 6, and vice versa). The columns 26 are configured to provide plastic deformation between the columns 26 and the screw head 32a. A first or primary measure of the plastic deformation is plastic deformation of the columns 26 from engagement with the screw head 32a. A second or secondary measure of the plastic deformation (i.e., plastic deformation of the screw head 32a, such as at least at the screw head threads 68a) can accompany the first measure of plastic deformation. Preferably, the first measure of plastic deformation at least exceeds the second measure of plastic deformation. More preferably, the second measure of plastic deformation is eliminated or at least minimized in favor of the first measure of plastic deformation. Stated differently, it is preferred that the screw head 32a deforms the columns 26 as opposed to the columns 26 deforming the screw head 32a. In this regard, the material of the plate body 9 is preferably selected so that the locking screw 8a comprises a material harder than the plate body 9 material. It is to be appreciated, however, that in operation a minor amount of plastic deformation of the screw head 32a (i.e., the second measure of plastic deformation) can occur. The geometry of the columns 26 as described herein provides the benefit of increasing the first measure of plastic deformation while decreasing the second measure of plastic deformation.

With continued reference to the plastic deformation, although the following description is made in reference to a single column 26, it is to be appreciated that additional columns 26 (and preferably each of the columns 26) within the aperture 6 will undergo the same or at least a substantially similar plastic deformation.

The internal threading slope A4 provides that, after the form-fit interaction is induced, further advancement of the screw head 32a causes the screw head threads 68a to press within the troughs of the internal thread portions 52 of the column 26 in a manner plastically deforming the engaged body 9 material at or adjacent the internal thread portions 52 and tightening the form-fit. Stated differently, the first measure of plastic deformation can commence at the internal aperture threading 50, which is further induced by the screw 8a material being harder than the plate body 9 material.

Yet further advancement of the screw head 32a within the aperture 6 causes the screw head threads 68a to engage the unthreaded lower column portion 62. The columns 26 are configured such that, as the screw head threads 68a engage the unthreaded lower column portion 62, the screw head threads 68a commence "thread-forming" the lower column portion 62 via plastically radially deforming the lower column portion 62 substantially without removing (e.g., shearing) body 9 material therefrom. In this manner, the first measure of plastic deformation continues within the lower column portion 62. The plastic deformation of the columns 26 can provide a tight locking press-fit between the plate body 9 and the screw head 32a within the aperture 6, locking the standard-type locking screw 8a to the plate body 9 at the nominal orientation. It is to be appreciated that the design of the columns 26 preferably avoids, or at least reduces, the occurrence of cross-threading because the thread forming of the columns 26 occurs in situ through engagement with the screw head threads 68a.

The columns 26 and the internal threading 50 are configured such that the first measure of plastic deformation occurs substantially in the radial direction R. However, it is to be appreciated that a minor degree of the first measure of plastic deformation can occur in a circumferential direction (i.e., the columns 26 can expand circumferentially into the recesses 28), and another minor degree of plastic deformation within portions of the columns 26 can occur vertically. It is also to be appreciated that a measure of elastic deformation beneficially accompanies the plastic deformation, so that the columns 26 reactively press radially inward against the screw head 32a, increasing the locking press-fit therebetween.

Figure 11:
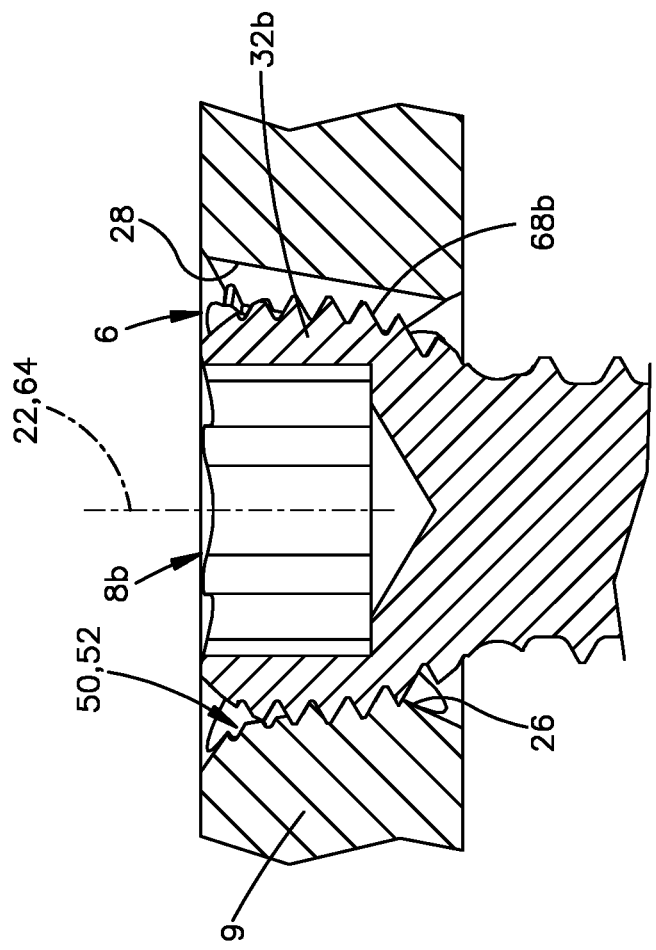
FIG. 11 is a sectional side view of the head of the variable-angle locking screw of FIG. 10 locked within an aperture of the bone plate of FIG. 7 at a nominal orientation.
Figure 10:
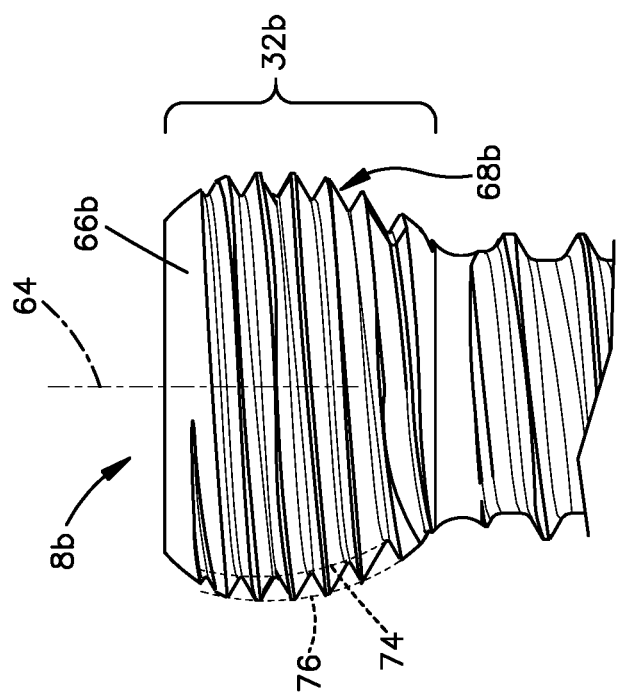
FIG. 10 is a side view of the head portion of a variable-angle locking screw configured to be locked within an aperture of a bone plate at either a nominal or angulated orientation.

Referring now to FIGS. 10 and 11, the columns 26 provide a similar locking function with the screw head 32b of a VA locking screw 8b at a nominal orientation. As shown in FIG. 10, the screw head 32b of the VA locking screw 8b can have a generally spherical outer surface 66b that defines external screw head threads 68b. The external screw head threads 68b of the VA locking screw 8b have a first threading profile 74 measured at the thread roots and a second threading profile 76 measured at the thread crests. As depicted, the threading profiles 74, 76 of the VA locking screw 8b are generally spherical, which provides the screw head 32b with a locking functionality as it advances within the aperture 6.

As shown in FIG. 11, similarly to the manner set forth above, as the screw head 32b of the VA locking screw 8b advances within the aperture 6, the screw head threads 68b commence a form-fit interaction with the column thread portions 52, which interaction leads to at least the first measure of plastic deformation (primarily in the radial direction R) as the head 32b advances further. Yet further screw head 32b advancement causes thread-forming of the unthreaded lower column portion 62 via plastic deformation thereof (primarily in the radial direction R) substantially without removing body material from the column 26, avoiding or reducing cross-threading. It is to be appreciated that the generally spherical profiles of the screw head 32b and the screw head threads 68b of the VA locking screw 8b can provide an increased plastic deformation relative to that of the standard-type locking screw 8a. It is also to be appreciated that a measure of elastic deformation beneficially accompanies the plastic deformation, so that the columns 26 reactively press radially inward against the nominal screw head 32b, increasing the locking press-fit therebetween.

Figure 12:
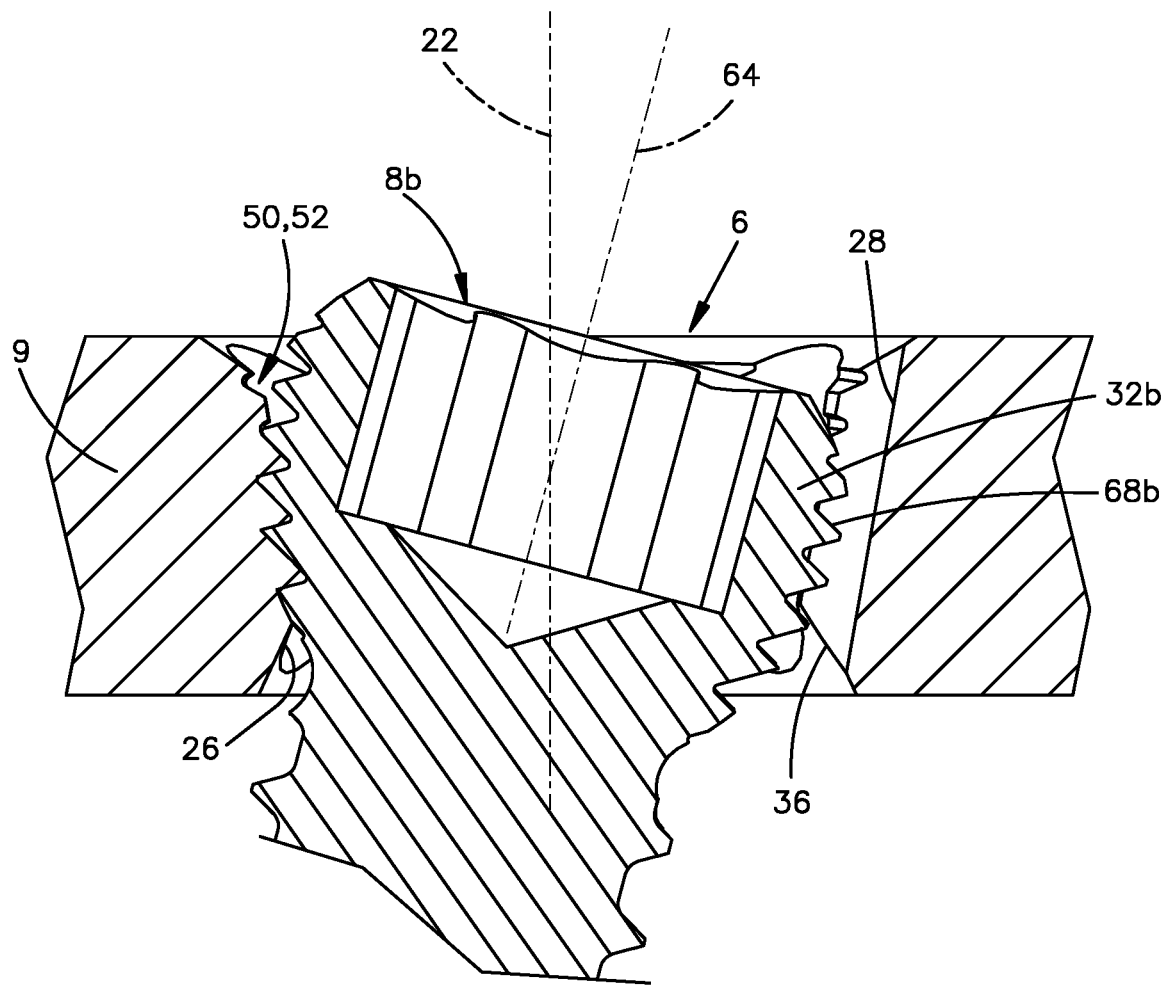
FIG. 12 is a sectional side view of the head of the variable-angle locking screw of FIG. 10 locked within an aperture of the bone plate of FIG. 7 at an angulated orientation.

Referring now to FIG. 12, the locking function of the columns 26 will now be discussed with reference to the VA locking screw 8b inserted along an angulated orientation within the aperture 6. In FIG. 12, the angulation is shown at about 15 degrees, whereby the relief angle allows the lower relief surface 36 to house a portion of the shaft of the screw 8b. As the angulated screw head 32b advances within the aperture 6, the head threads 68b commence a form-fit interaction with the column thread portions 52, which interaction is enabled at least in part by the pitch, thread angle, and/or the slope A4 of the column thread portions 52 and the pitch, thread angle, and/or the generally spherical profile of the head threads 68b as well as the particular angulated orientation. The form-fit interaction leads to at least the first measure of plastic deformation (primarily in the radial direction R) as the screw head 32b advances. Yet further screw head 32b advancement at the angulated orientation causes thread forming of the unthreaded lower column portion 62 via plastic deformation thereof (primarily in the radial direction R), which, as described above, can occur substantially without removing body material from the column 26. It is to be appreciated that, as above, a measure of elastic deformation beneficially accompanies the plastic deformation, so that the columns 26 reactively press radially inward against the angulated screw head 32b, increasing the locking press-fit therebetween.

Another embodiment of the locking structures will now be described with reference to FIGS. 13 through 20. For the sake of brevity, the following description will focus mainly on the differences between the present embodiments and the embodiments described above with reference to FIGS. 1 through 12.

Figure 13:
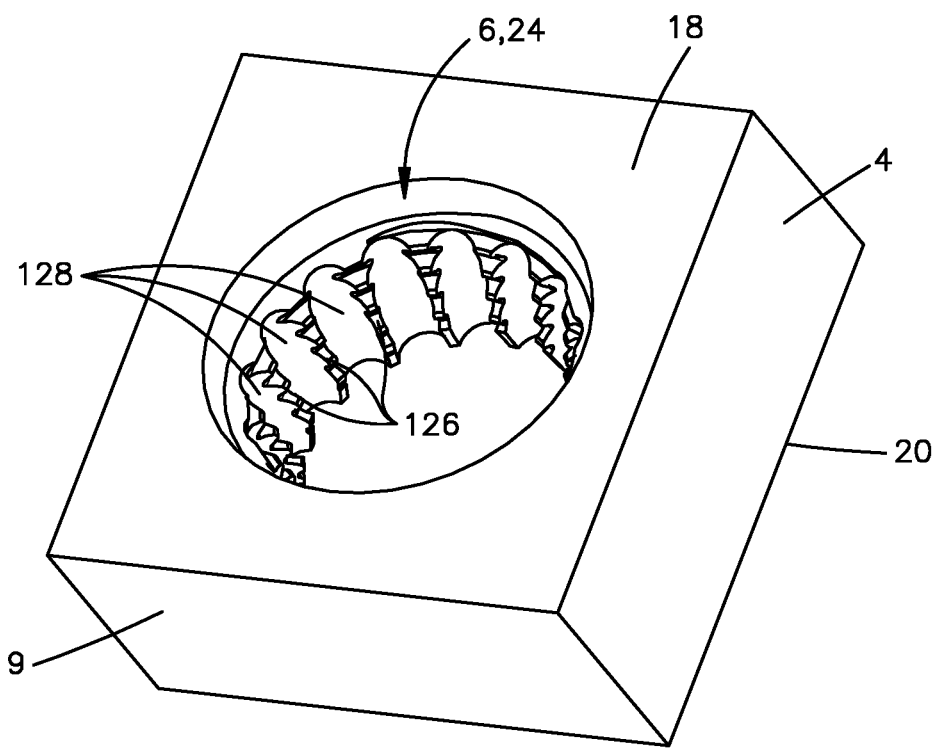
FIG. 13 is a perspective view of an aperture of a bone plate, with locking structures within the aperture, according to another embodiment of the present disclosure.

Referring now to FIG. 13, the locking structures include a plurality of columns 126 and a plurality of recesses 128 sequentially located about the circumference of the interior surface 24 of the aperture 6. The columns 126 extend vertically between the upper and lower plate surfaces 18, 20 and are configured to deform primarily in the radial direction R responsive to engagement with a head of a locking screw. As described above, compression of the columns 126 around the screw head forms a tight press-fit therebetween, locking the screw head within the aperture 6 at a fixed orientation with respect to the bone plate 4.

Figure 14:
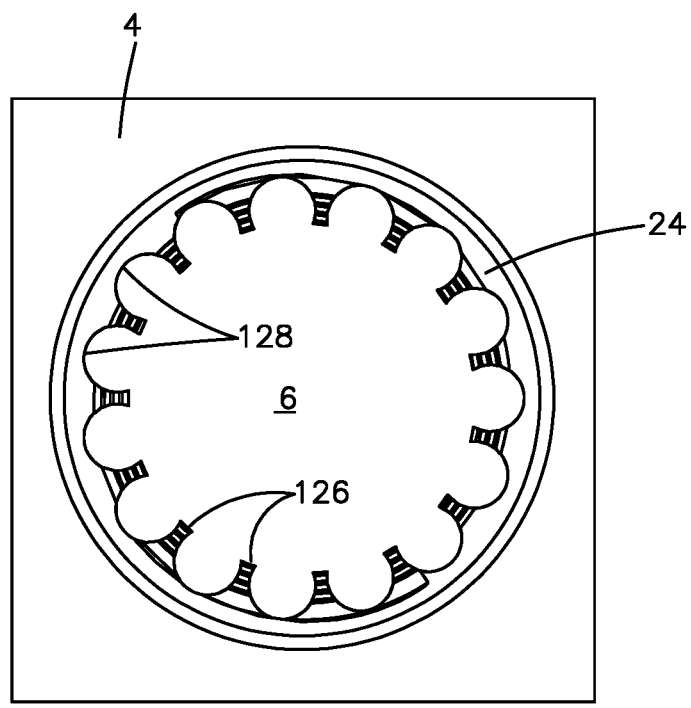
FIGS. 14 and 15 are top and bottom views, respectively, of the aperture of FIG. 13.

Referring now to FIG. 14, the columns 126 and recesses 128 can be evenly spaced about the circumference of the interior surface 24, as shown; although un-even spacing can be employed in other embodiments. The interior surface 24 can define fifteen (15) columns 126 and fifteen (15) recesses 128, although less than fifteen (15) or more than fifteen (15) columns 126 and recesses 128 can also be employed.

Figure 16:
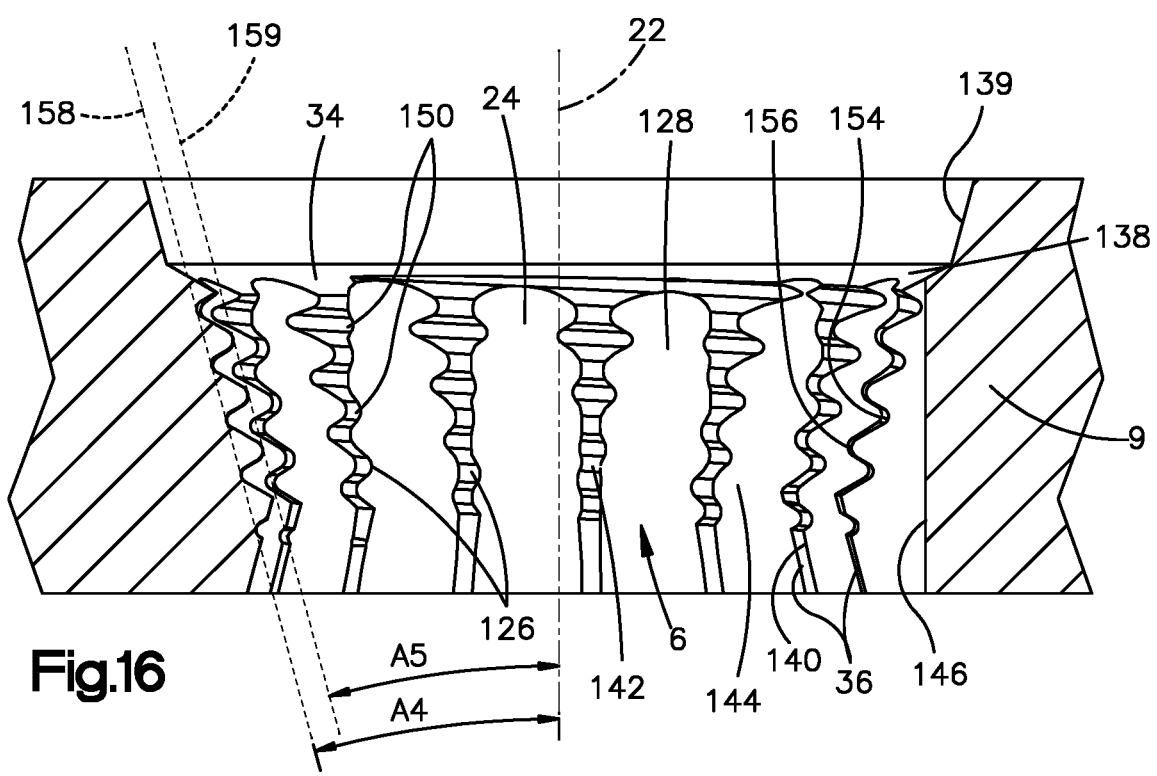
FIG. 16 is a sectional side view of the aperture of FIG. 13.

In the present embodiment, the recesses 128 can each extend purely vertically, or at least substantially vertically, between an upper relief surface 34 and a lower relief surface 36 defined by the interior surface 24, as shown in FIG. 16. In this manner, the nadirs 146 of the recesses 128 can be parallel with the central aperture axis 22; additionally, the radius of each recess 128 in a horizontal reference plane can be the same at any vertical location within the recess 128. In other embodiments, the recesses 128 can be angled with respect to the central aperture axis 22, similar to the manner described above with reference to FIG. 4. The recesses 128 can optionally be sized and located such that, in a horizontal reference plane, each column 126 is thicker at its first or innermost surface 142 that at a radially outward location of its side surfaces 144. In the present embodiment, the upper relief surface 34 can define a relief angle in a range of about 0 degrees to about 85 degrees and the lower relief surface 36 can define a relief angle in a range of about 0 degrees to about 60 degrees.

Figure 15:
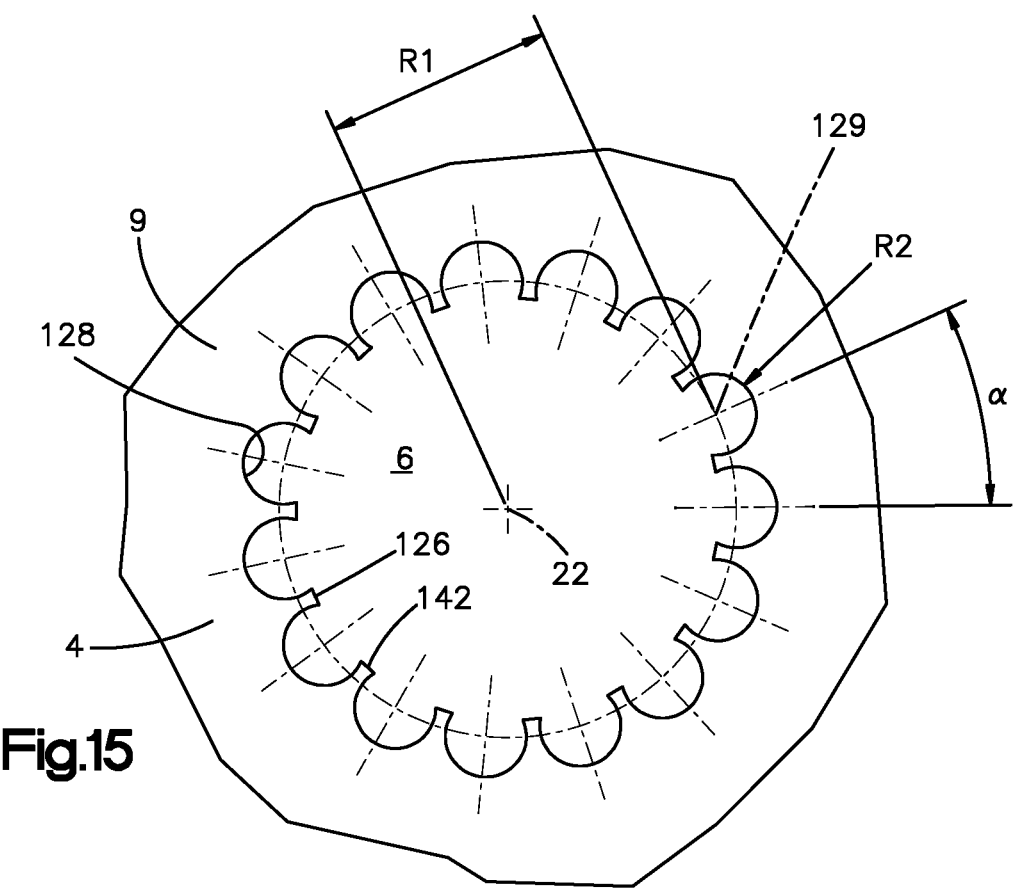

Referring now to FIG. 15, in one example of the present embodiment, the aperture 6 can include fifteen (15) recesses 128 with central recess axes 129 spaced at 24 degree intervals a about the central aperture axis 22. In this example, the central recess axes 129 are located radially outward of the first surfaces 142 of the columns 126, and are spaced from the central aperture axis 22 by a radial distance R1 in a range of about 1.8 mm to about 2.7 mm and preferably about 2.25 mm. Also in this example, each recess 128 defines a recess radius R2 in a range of about 0.2 mm to about 0.6 mm and preferably about 0.4 mm.

Referring now to FIG. 16, the upper relief surface 34 can define upper ends 138 of the columns 126 and the lower relief surface 36 can define lower ends 140 of the columns 126, as described above. The first surface 142 of each column 126 extends between the upper and lower ends 138, 140 and substantially faces the central aperture axis 22. The side surfaces 144 of each column 126 can define at least portions of the circumferentially adjacent recesses 128. The aperture 6 can also include a second upper relief surface 139, which can be a countersink, for example.

In the present embodiment, the internal aperture threading 150 can extend from a location within the upper relief surface 34 to a location within the lower relief surface 36. In this manner, the internal aperture threading 150 can helically traverse one or more of the columns 126 from its upper end 138 to its lower end 140. The threading 150 can include thread crests 156 that define the first surface 142 of each columns 126 and roots 154 recessed radially outward from the first surface 142. The internal threading 150 can define a thread angle A3 in a range of about 30 degrees to about 90 degrees, preferably in the range of about 55 degrees to about 65 degrees, and more preferably at about 60 degrees. The thread portions 52 can define a thread pitch in a range of about 0.1 mm to about 1.6 mm, and more preferably at about 0.8 mm, by way of non-limiting examples. The threading 150 is preferably a right-hand thread, although left-hand threading 150 is within the scope of the present disclosure. The threading 150 can be dual-lead, as shown, although single-lead threading 150 is also within the scope of the present disclosure. The first and second upper relief surfaces 34, 139 can provide that the top of the internal threading 150 is recessed from the upper plate surface 18, which enhances the smoothness of the upper plate surface 18 and can eliminate soft tissue irritation from un-used apertures 6. The first upper relief angle also facilitates smoother initial engagement between the screw head thread 68 and the lead of the internal threading 150.

The internal threading 150 can define a first threading profile 158 extending along the thread roots 154 and a second threading profile 159 extending along the thread crests 156. As shown, the first and second threading profiles 158, 159 can be substantially parallel, providing the threads of the internal threading 150 with substantially equivalent thread depths. However, in other embodiments, the first and second threading profiles 158, 159 can be non-parallel, and the thread depths of the internal threading 150 can vary. With continued reference to FIG. 16, the first and second threading profiles 158, 159 can extend at respective angles A4, A5 each in a range of about 5 degrees to about 60 degrees from the central aperture axis 22, preferably from about 10 degrees to about 20 degrees, and more preferably about 15 degrees.

The first surfaces 142 of the columns 126 (along second threading profile 159) can collectively define segments of a first shape, such as an inverted frusto-conical shape. The nadirs 146 of the recesses 128 can collectively define segments of a second shape, such as cylindrical shape. The columns 126 and recesses 128, respectively, can be configured to collectively define other shapes, as described above with reference to FIGS. 4 and 5. Additionally, the first surfaces 142 of the columns 126 of the present embodiment have a concave profile in a horizontal reference plane, although in other embodiments the first surfaces 142 can have convex or linear profiles in a horizontal reference plane.

With reference to FIGS. 17 through 20, engagement between the apertures 6 and a VA locking screw 8b at various angulations will now be described. The VA locking screw 8b of the present embodiment can be configured similarly to that described above.

Referring now to FIG. 17, at a nominal orientation, the internal threading 150 of the aperture 6 is configured to engage the screw head threads 68b in an interconnecting manner so as to substantially induce a form-fit interaction therebetween (i.e., the apices of the external screw head threads 68a extend within the troughs of the interior aperture threading 150, and vice versa). The threading profiles 158, 159 of the internal threading 150 and the threading profiles 74, 76 of the screw head threads 68b provide that, after the form-fit interaction is induced, further advancement of the screw head 32b causes the screw head threads 68b to press within the troughs of the internal threading 150 of the column 126 to lock the screw head 32b to the plate 4 substantially without deformation.

Figure 20:
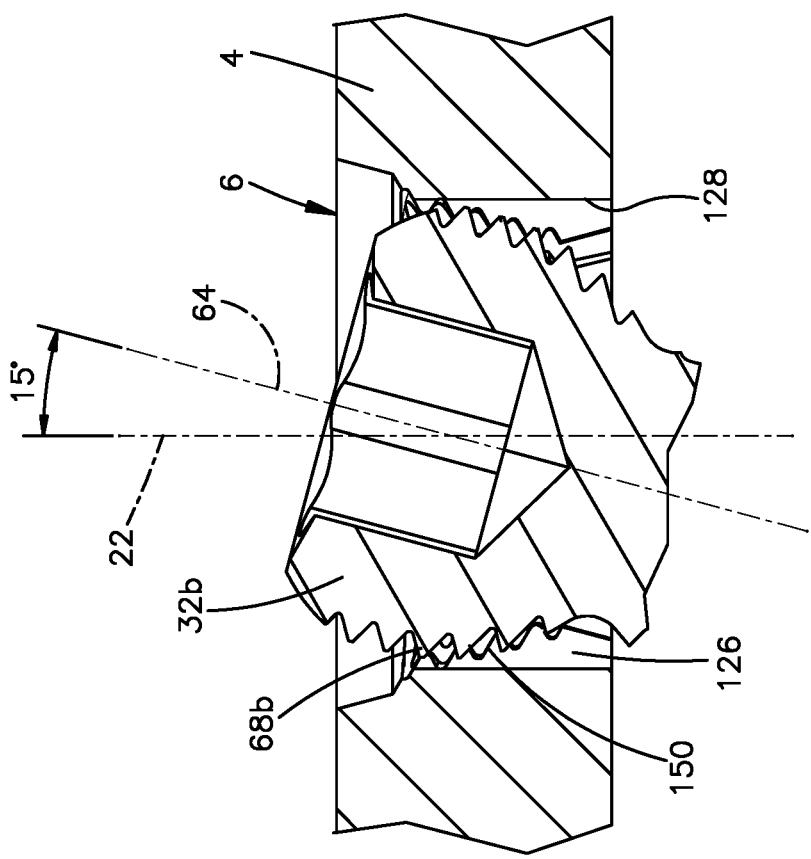
FIG. 20 is a section view of the variable-angle locking screw locked within the aperture of FIG. 16 at an angulation of about 15 degrees.
Figure 19:
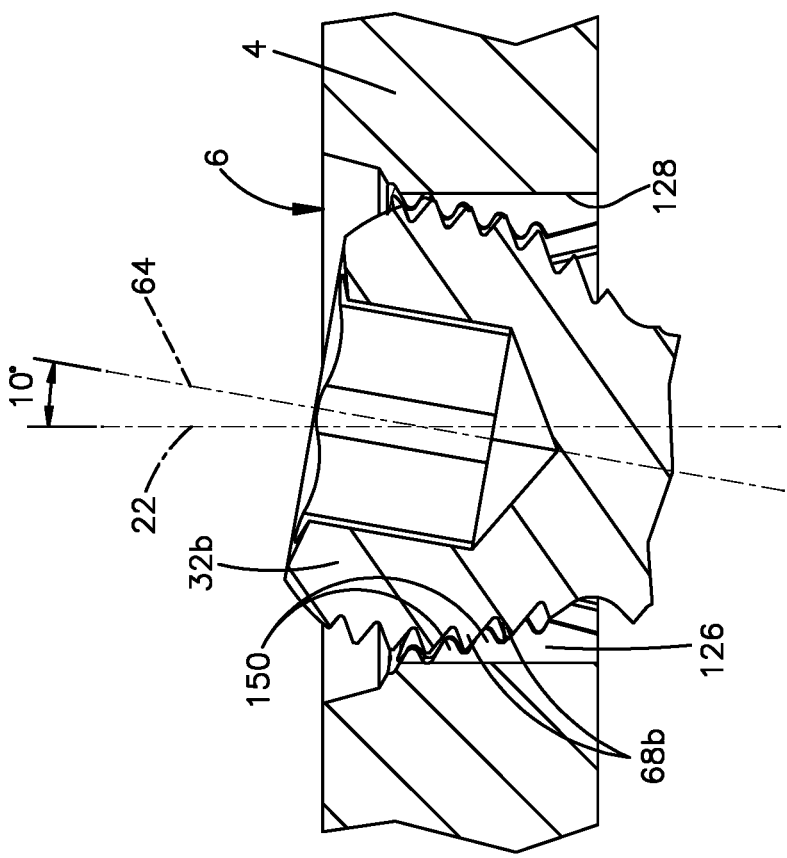
FIG. 19 is a section view of the variable-angle locking screw locked within the aperture of FIG. 16 at an angulation of about 10 degrees.

Referring now to FIGS. 18 through 20, the columns 126 are configured such that, at varying angulations, such as at 5 degrees (FIG. 18), at 10 degrees (FIG. 19), and at 15 degrees (FIG. 20), as the angulated screw head 32b advances within the aperture 6, the screw head threads 68b commence a form-fit interaction with the column threading 150. This initial form-fit interaction is enabled at least in part by the pitch, thread angle, and/or the threading profiles 158, 159 of the internal threading 150 and the pitch, thread angle, and/or the generally spherical profiles 74, 76 of the screw head threads 68b, as well as the angulation. After the form-fit interaction is induced, further advancement of the angulated screw head 32b causes the screw head threads 68b to elastically and plastically deform the columns 126, primarily at the internal threading 150. This compresses the columns 126 and causes the columns 126 to exert a reactive compressive force against the screw head 32b, together providing a locking compression fit between the columns 126 and the screw head 32b. The columns 126 are configured so that the angulated screw head 32b can be fully seated within the aperture 6 substantially without cross-threading the columns 150, although some minor cross-threading may occur in some instances. The columns 126 are also configured such that, even at increased angulations, the columns 126 deform primarily in the radial direction R, although some circumferential and/or vertical deformation can also occur. It is to be appreciated, however, that as the angulation increases, the extent of circumferential and/or vertical deformation can also increase. The foregoing modes of deformation of the columns 126 allows VA locking screws 8b to be inserted at angulated orientations substantially without cross-threading the internal threading 150 or the screw head threads 68b.

Figure 21:
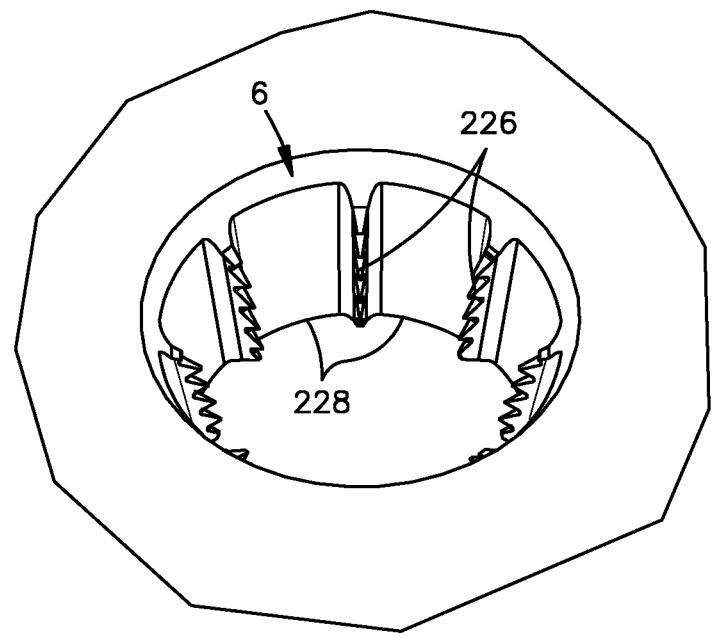
FIG. 21 is a perspective view of an aperture of a bone plate, with locking structures within the aperture, according to another embodiment of the present disclosure.
Figure 22:
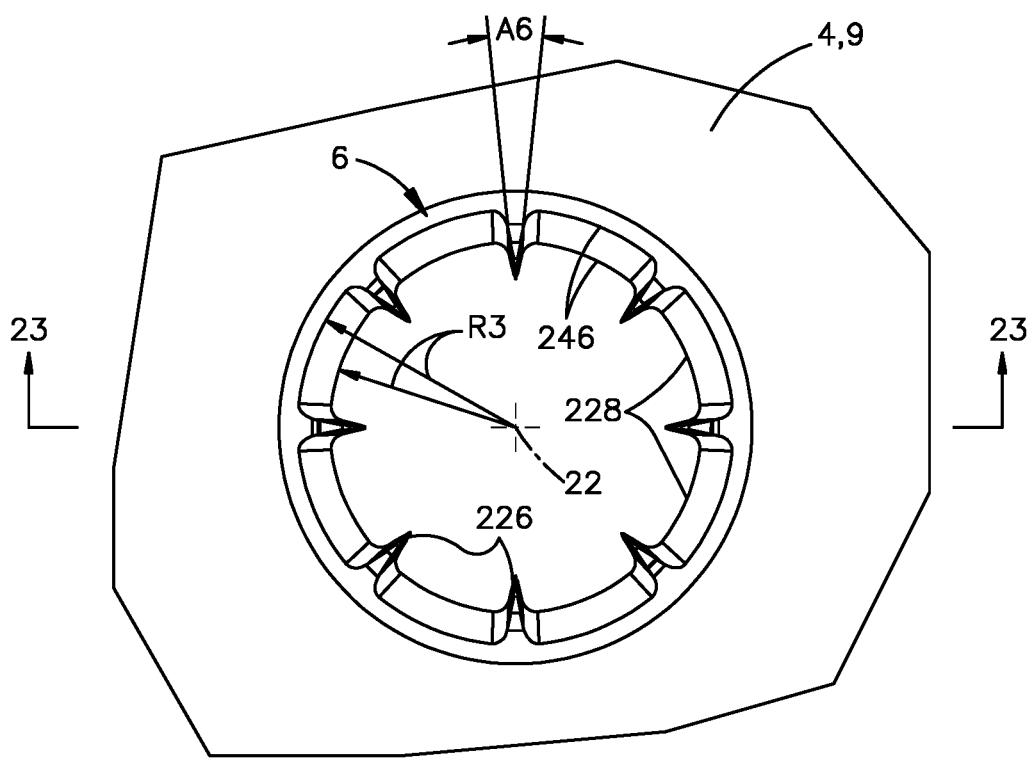
FIG. 22 is a top plan view of the aperture shown in FIG. 21.
Figure 23:
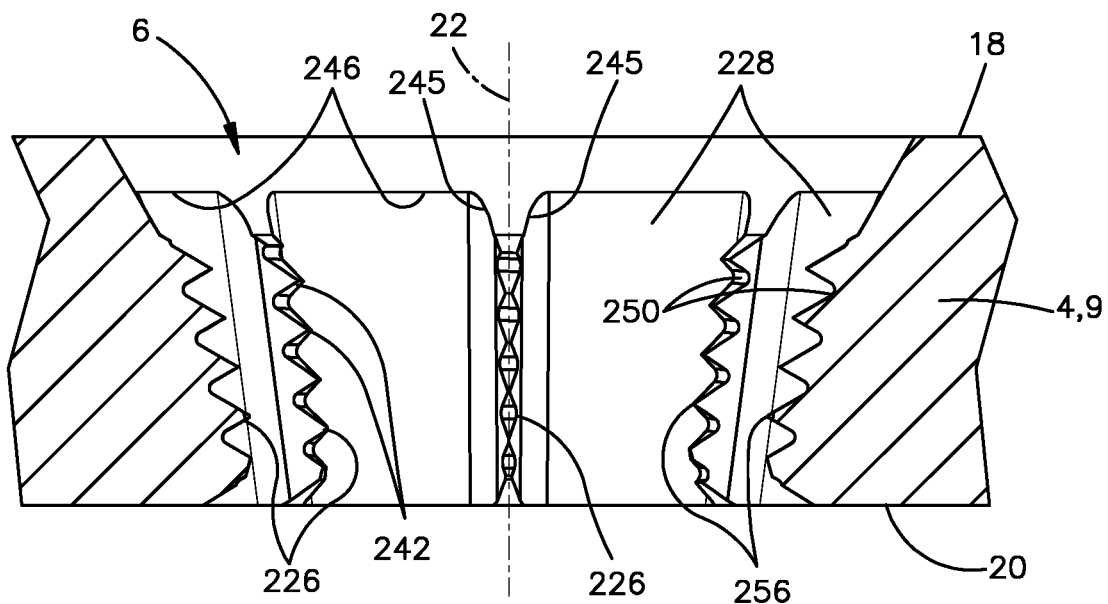
FIG. 23 is a sectional side view of the aperture taken along section line 23-23 in FIG. 22.

Referring now to FIGS. 21 through 23, in another embodiment, the locking structures in the apertures 6 can include columns 226 that are circumferentially thinner than the columns 26, 126 of the previous embodiments and recesses 228 that are circumferentially wider than the recesses 28, 128 of the previous embodiments. The recesses 228 can define nadirs 246 that extend circumferentially between adjacent columns 226 at a substantially constant radius R3 measured from the central aperture axis 22 in any horizontal reference plane intersecting the nadirs 246. The nadirs 246 can collectively define an inverted frusto-conical shape. The columns 226 can each define an innermost first surface 242 and side surfaces 245 that extend radially between the first surface 242 and the adjacent nadirs 246. The side surfaces 245 can each be substantially planar and can be oriented at an angle A6 in a range of about 10 degrees to about 45 degrees with respect to each other, and preferably at an angle A6 in a range of about 20 degrees to about 30 degrees with respect to each other. The first surface 242 can decrease in circumferential width moving vertically from the upper plate surface 18 toward the lower plate surface 20. The columns 226 can define internal aperture threading 250 with threading characteristics (e.g., thread angle, pitch, threading profile(s), and lead type (i.e., single-, double-, or triple-lead)) similar to those described above. In the lower region of the aperture 6, the crests 256 of the internal aperture threading 250 can define substantially pointed tips.

The columns 226 are configured such that, when a locking screw 8a, 8b is inserted in the aperture 6 at a nominal orientation, the screw head threads 68a, 68b engage the internal aperture threading 250 in an interconnecting manner so as to substantially induce a form-fit interaction therebetween. After the form-fit interaction is induced, further advancement of the screw head 32a, 32b causes the screw head threads 68a, 68b to press within the troughs of the internal aperture threading 250 of the columns 226 to lock the screw head 32a, 32b to the plate 4 substantially without deformation. At angulated orientations of the VA locking screw 8b, advancement of the screw head 32b within the aperture 6 commences a form-fit interaction with the internal aperture threading 250, and further advancement causes the screw head threads 68b to elastically and plastically deform the columns 226, primarily at the internal aperture threading 250, in a manner providing a locking compression fit between the columns 226 and the screw head 32b, similar to the manner described above, substantially without cross-threading.

Figure 24:
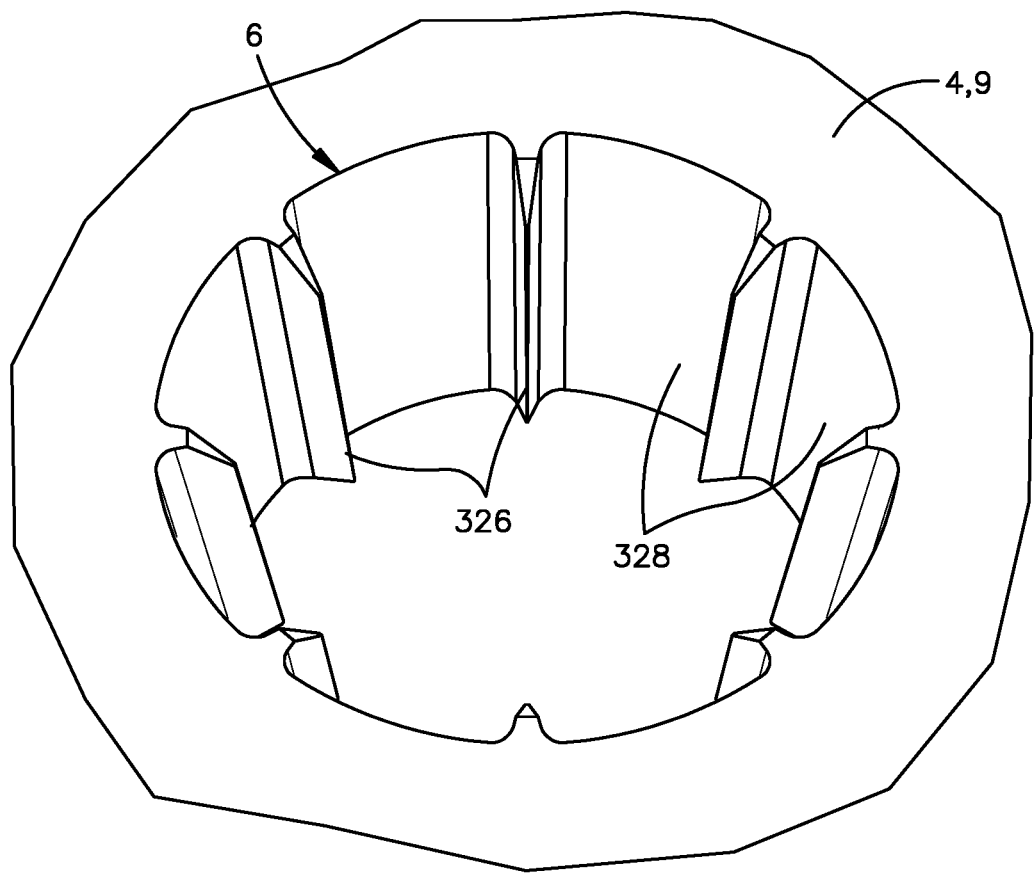
FIG. 24 is a perspective view of an aperture of a bone plate, with locking structures within the aperture, according to another embodiment of the present disclosure.
Figure 25:
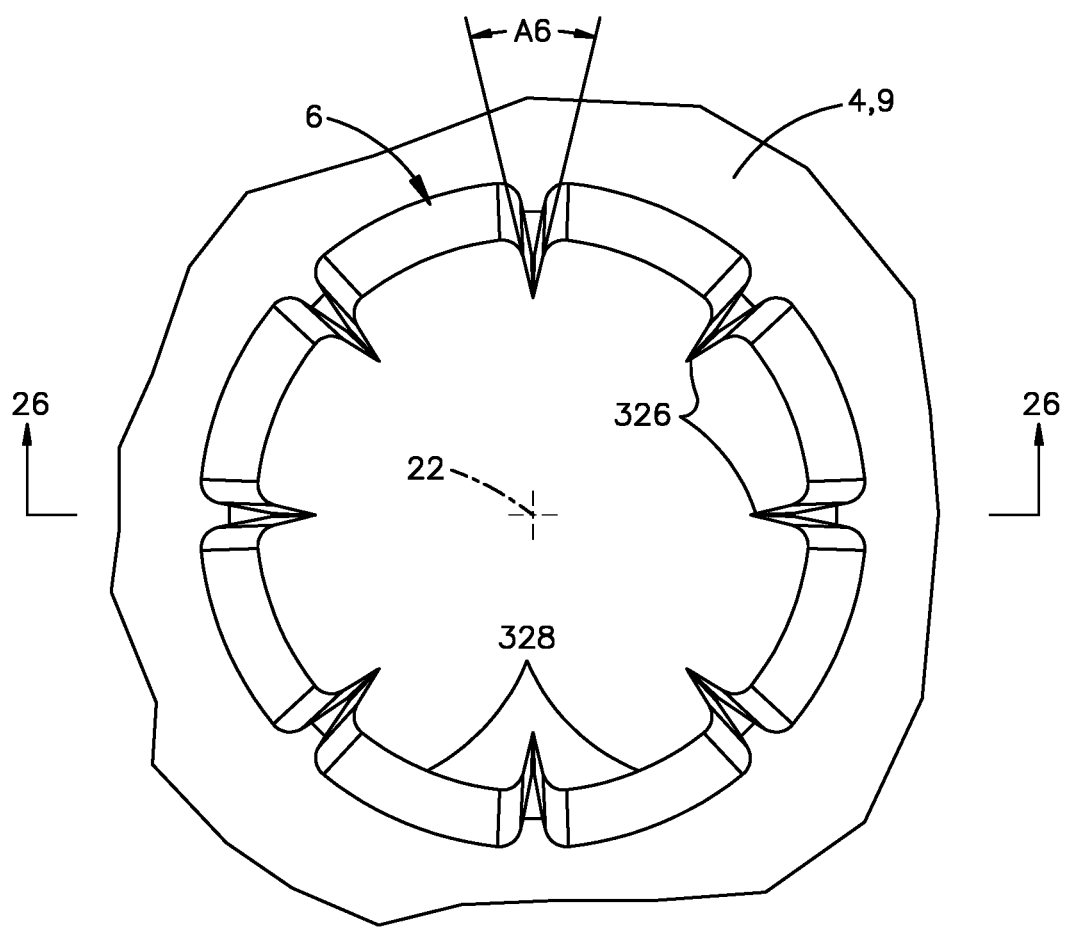
FIG. 25 is a top plan view of the aperture shown in FIG. 24.
Figure 26:
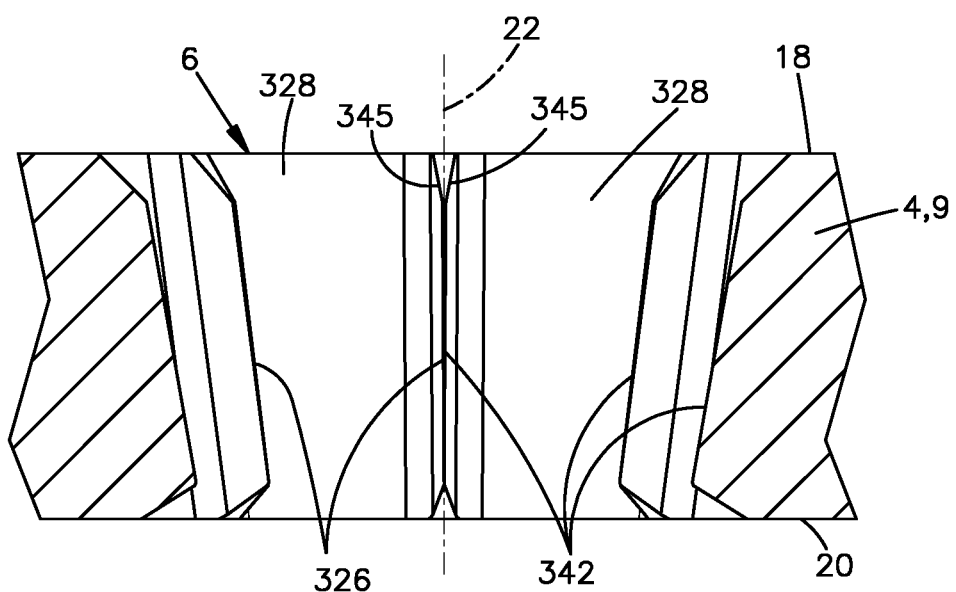
FIG. 26 is a sectional side view of the aperture taken along section line 26-26 in FIG. 25.

Referring now to FIGS. 24 through 26, the apertures 6 can define columns 326 and recesses 328 that are similar to those described above with reference to FIGS. 21 through 23. However, the columns 326 of the present embodiment can be unthreaded (i.e., can be devoid of threading). Side surfaces 345 of each column 326 can be substantially planar and can be oriented at an angle A6 in a range of about 10 degrees to about 45 degrees with respect to each other, and preferably at an angle A6 in a range of about 20 degrees to about 30 degrees with respect to each other. The first surfaces 342 of the columns 326 can each decrease in circumferential width moving vertically from the upper plate surface 18 toward the lower plate surface 20 so as to taper to a single edge in a lower region of the aperture 6. In this embodiment, as the screw head 32a, 32b advances within the aperture 6 (whether at nominal or angulated orientations), the screw head threads 68a, 68b plastically and elastically deform the columns 326 radially and in a thread-forming manner so as to provide a locking compression fit between the columns 326 and the screw head 32a, 32b.

It is to be appreciated that, in further embodiments, the columns 26, 126, 226, 326 described herein can be defined by an insert disposed within an aperture 6 in a bone plate 4. In such embodiments, the columns 26, 126, 226, 326 of the insert, the screw head, and the plate 4 itself can each be configured to deform plastically in a manner locking the screw 8 to the plate 4.

Figure 27:
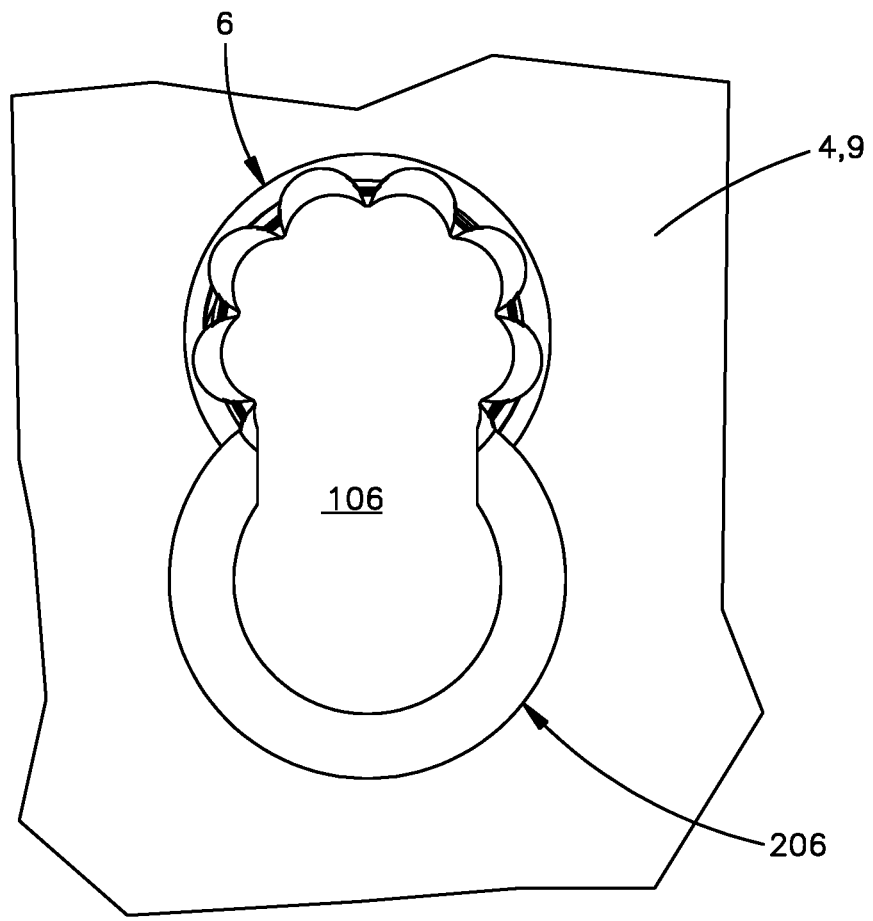
FIG. 27 is a top plan view of an aperture, according to an embodiment of the present disclosure, in which the aperture is intersected by an additional aperture so as to define a "combi-hole".

Referring now to FIG. 27, the bone plate 4 can be configured such that one or more of the apertures 6 is intersected by another structure, such as another aperture 206, by way of non-limiting example. As shown, an aperture 6 can be intersected by a second aperture 206 in a manner collectively defining a "combi-hole" 106. It is to be appreciated that other aperture configurations are also within the scope of the present disclosure.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. A bone plate, comprising:
an upper surface configured to face away from a bone and an opposed lower surface configured to face the bone; and
at least one aperture extending through the bone plate from the upper surface to the lower surface along a central aperture axis, the at least one aperture defined by an interior surface of the bone plate, the interior surface further defining a plurality of columns sequentially located about a circumference of the interior surface and a plurality of recesses located circumferentially between the columns, wherein each of the columns is configured to undergo deformation at least in a radial direction perpendicular to the central aperture axis responsive to engagement with a head of a locking bone screw receivable within the at least one aperture so as to lock the head to the bone plate, and the plurality of columns comprises at least five columns.

2. The bone plate of claim 1, wherein the deformation includes plastic deformation, and the columns are configured such that the plastic deformation reduces cross-threading of the columns.

3. The bone plate of claim 1, wherein the plurality of columns comprises at least nine columns.

4. The bone plate of claim 1, wherein the columns are evenly spaced about the circumference of the interior surface.

5. The bone plate of claim 1, wherein each column defines a first surface substantially facing the central aperture axis, and a pair of side surfaces located on adjacent circumferential sides of the first surface, the pair of side surfaces at least partially defining a respective pair of the recesses on the adjacent circumferential sides of the first surface.

6. The bone plate of claim 5, wherein at least one of the first surfaces of the plurality of columns has a convex profile in a reference plane orthogonal to the central aperture axis.

7. The bone plate of claim 5, wherein at least one of the first surfaces of the plurality of columns has a concave profile in a reference plane orthogonal to the central aperture axis.

8. The bone plate of claim 5, wherein the first surfaces of each of the columns taper radially inwardly from the upper surface to the lower surface at an angle in a range of about 3 degrees to about 30 degrees to the central aperture axis.

9. The bone plate of claim 5, wherein the at least one aperture includes internal threading that helically traverses the plurality of columns such that each column defines one or more thread portions of the internal threading, and the one or more thread portions of at least some of the columns are configured to undergo at least some of the deformation when the head of the locking bone screw is inserted.

10. The bone plate of claim 9, wherein the internal threading is tapered along a taper axis that extends along roots of the internal threading and is oriented such that the taper axis and the central aperture axis are each coextensive in a common reference plane, and the taper axis is angled radially inwardly from the upper surface to the lower surface at an angle in a range of about 4 degrees to about 40 degrees to the central aperture axis.

11. The bone plate of claim 10, wherein the internal threading is configured such that each column defines an upper column portion defining the one or more thread portions and a lower column portion having no threading, the lower column portion is configured to be deformed by external threads of the screw head, and the deformation occurs substantially without removal of material from the respective column.

12. The bone plate of claim 1, wherein the interior surface of the aperture further defines a lower relief surface extending upward from the lower surface of the bone plate toward the upper surface and the relief surface defines a portion of each of the columns.

13. The bone plate of claim 12, wherein the internal threading helically traverses the columns from an upper end of each column to the lower relief surface.

14. The bone plate of claim 1, wherein the recesses are each angled radially inwardly from the upper surface to the lower surface at an angle in a range of about 0 degrees to about 30 degrees to the central aperture axis.

15. The bone plate of claim 1, wherein the recesses are each oriented substantially parallel to the central aperture axis.

16. The bone plate of claim 1, wherein the at least one aperture intersects another aperture, and the at least one aperture and the another aperture collectively define a combi-hole.

17. A system for affixation to one or more portions of bone, the system comprising:
   the bone plate of claim 1; and
   one or more locking bone screws that are each insertable within the at least one aperture at one or more of a nominal angle and a variable angle.

18. The system of claim 17, wherein the one or more locking bone screws includes one or more variable angle bone screws.

19. The system of claim 18, wherein the one or more locking bone screws comprises a plurality of locking bone screws, and the plurality of locking bone screws includes locking bone screws having different shapes, different sizes, or different shapes and different sizes.

20. The system of claim 17, wherein the one or more locking bone screws are made from a first material, and the bone plate is made from a second material, wherein the first material is harder than the second material.

* * * * *